United States Patent
Seeber et al.

(10) Patent No.: US 7,199,161 B2
(45) Date of Patent: *Apr. 3, 2007

(54) SUBSTITUTED BICYLO[3.3.1]NONAN-2,4,9-TRIONES AS PHARMACEUTICAL ACTIVE INGREDIENTS

(75) Inventors: Siegfried Seeber, Essen (DE); Ralf Axel Hilger, Eneppetal (DE); David Diaz-Carballo, Essen (DE)

(73) Assignee: Diagenics International Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/496,593

(22) PCT Filed: Nov. 20, 2002

(86) PCT No.: PCT/EP02/12967

§ 371 (c)(1),
(2), (4) Date: Oct. 29, 2004

(87) PCT Pub. No.: WO03/043622

PCT Pub. Date: May 30, 2003

(65) Prior Publication Data

US 2005/0090693 A1    Apr. 28, 2005

(30) Foreign Application Priority Data

Nov. 21, 2003  (EP) ................... 10157033

(51) Int. Cl.
*A61K 31/12* (2006.01)
*A61K 31/05* (2006.01)
*C07C 49/00* (2006.01)

(52) U.S. Cl. ............ 514/690; 514/732; 568/375; 568/377

(58) Field of Classification Search ........... 568/375, 568/377; 514/690, 732
See application file for complete search history.

(56) References Cited

OTHER PUBLICATIONS

Porto et al. Polyisoprenylated benzophenones from Clusia floral resins. Phytochemistry. 55, 2000, p. 755-768.*
Oliveira et al. Floral Resins of Clusia SPP.: Chemical Composition and Biological Function.□□Tetraheron Letters, vol. 37 (36), 1996, p. 6427-6430.*
Henry et al. Prenylated Benzophenone Derivatives from Carribean Clusia species (Guttiferae).□□Tetrahedron, vol. 55, 1999, p. 1581-1596.*

* cited by examiner

*Primary Examiner*—Sikarl A. Witherspoon
(74) *Attorney, Agent, or Firm*—Bachman & LaPointe, P.C.

(57) ABSTRACT

The invention relates to the use of substituted bicyclo[3.3.1] nonan-2,4,9-triones, especially clusianon and clusianon derivatives, as pharmaceutical active ingredients or medicamentous active ingredients, especially for producing medicaments for the prophylactic and/or therapeutic (curative) treatment of tumour or cancer diseases, and of viral diseases. The above-mentioned compounds can be used in cytostatic agents and antiviral agents (virostatic agents). They are especially used as inhibitors of topoisomerases and telomerases and as regulators during the MAP kinase signal transduction and can thus intervene on a cellular scale in the mechanism for multiplication of tumour or cancer cells and viruses.

7 Claims, 22 Drawing Sheets

| Column 1 (controls) | Column 2 (substance (I)) |
|---|---|
| positive control | positive control |
| negative control | negative control |
| 20 ng cell nucleus extract | 1.56 g/ml substance (I) |
| 40 ng cell nucleus extract | 3.12 g/ml substance (I) |
| 80 ng cell nucleus extract | 6.24 g/ml substance (I) |
| 160 ng cell nucleus extract | 12.5 g/ml substance (I) |
| 320 ng cell nucleus extract | 25.0 g/ml substance (I) |
| 640 ng cell nucleus extract | 50.0 g/ml substance (I) |
| 1280 ng cell nucleus extract | 100 g/ml substance (I) |

Fig. 2

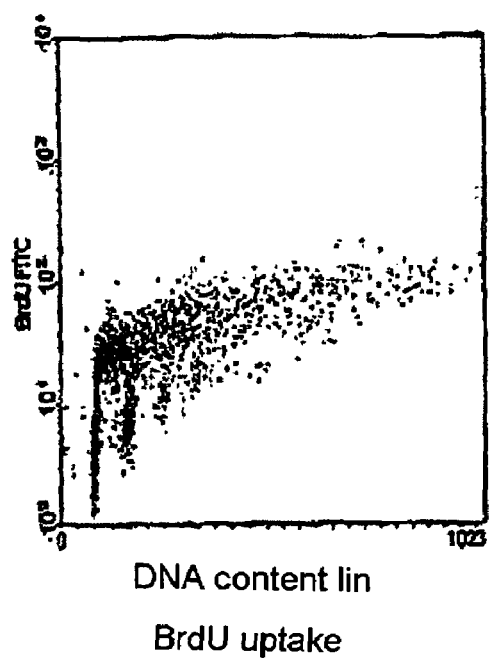 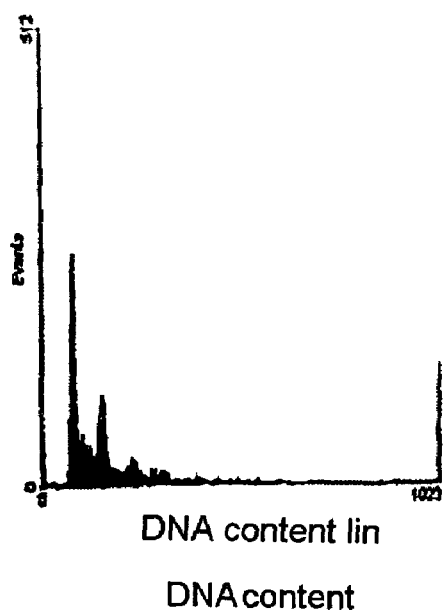
DNA content lin  
BrdU uptake
DNA content lin  
DNA content
Fig. 3a
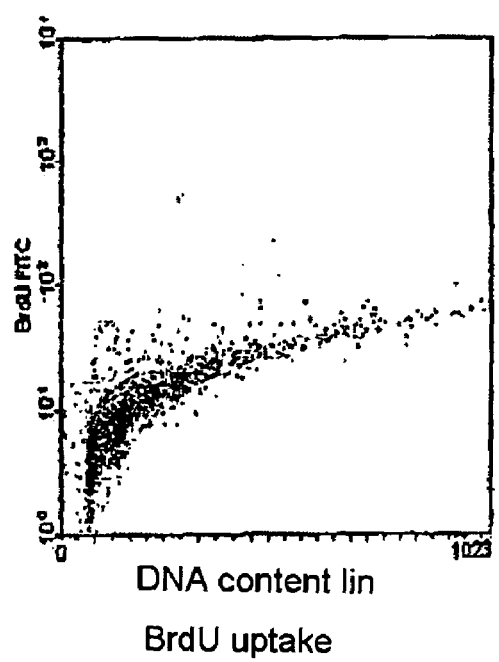 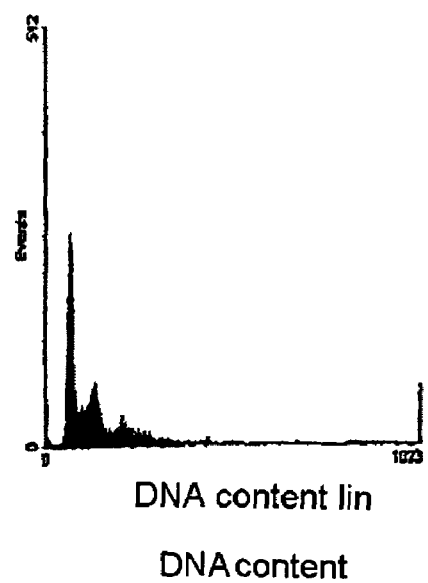
DNA content lin  
BrdU uptake
DNA content lin  
DNA content
Fig. 3b

SUBSTITUTED BICYLO[3.3.1]NONAN-2,4,9-TRIONES AS PHARMACEUTICAL ACTIVE INGREDIENTS

This application is the national stage of PCT/EP02/12967 filed Nov. 20, 2002, and published as WO 03/043622 on May 30, 2003.

BACKGROUND OF THE INVENTION

The present invention relates to the use of substituted bicyclo[3.3.1]nonane-2,4,9-triones, in particular clusianone and clusianone derivatives, as active pharmaceutical ingredients or active ingredients of medicaments, in particular for producing medicaments for the prophylactic and/or therapeutic (curative) treatment of neoplastic or cancerous diseases and of viral diseases. The present invention equally relates to substituted bicyclo[3.3.1]nonane-2,4,9-triones as pharmaceutically active ingredients of medicaments or pharmaceutical compositions, in particular cytostatics and antiviral compositions (virustatics). The present invention further relates to the use of substituted bicyclo[3.3.1]nonane-2,4,9-triones as topoisomerase inhibitors and/or telomerase inhibitors and as regulators within MAP kinase signal transduction.

Neoplastic or cancerous diseases are not a single pathological state but are generic terms for a large number of different types of malignant diseases. Virtually every tissue in the body may give rise to cancerous degenerations, and sometimes even to several different types. Each of the disorders in turn has its own features. The causes leading to these diseases are often very heterogeneous.

Despite this diversity, virtually all tumors and cancerous degeneration arise through very similar fundamental molecular or cellular processes. Research in the last two decades has made astonishing advances in knowledge concerning the most fundamental processes of carcinogenesis and tumorigenesis at the molecular level.

The genetic information is carried by the DNA molecules of the chromosomes in the cell nucleus. Two classes of genes which together account for only a small fraction of the total endowment of a cell play an essential role in the development of cancer, namely in particular proto-oncogenes (cancer gene precursors) and tumor suppressor genes (genes which suppress tumors). In their normal form, they direct the life cycle of the cell, they control the complicated sequence of processes by which a cell becomes larger and, if required, divides. Whereas proto-oncogenes promote cell growth, it is retarded by tumor suppressor genes. Together, these two classes of genes are responsible for a large part of the uncontrolled cellular proliferation processes in human tumors: if, for example, a proto-oncogene mutates in the regulatory region or in the structural region, it is possible that there is then production of too much of its growth-promoting protein, or that the latter is then excessively active; the proto-oncogene has become a cancer-favoring oncogene which stimulates the cells to excessive proliferation. By contrast, tumor suppressor genes contribute to the development of cancer if they are inactivated by mutations; as a consequence, the cell loses suppressor proteins capable of functioning, and thus crucial growth retarders which normally prevent it from inappropriate proliferation.

An emergency mechanism against unlimited proliferation is incorporated into normal body cells, and comprises a type of counter which records every cell division and calls a halt after a certain number of generations. After a certain number, which can be approximately predicted, of cell divisions or doublings, growth of normal cells ceases. This process is referred to as cell aging or senescence.

Responsible at the molecular level for this process of cell aging or senescence are the DNA fragments at the ends of the chromosomes, called the telomeres. They record as it were how many proliferation cycles a cell population experiences and, after a particular time, initiate senescence or the crisis. In this way they limit the ability of a cell population to grow unrestrictedly. In most healthy human cells, the telomeres are shortened by a small piece when the chromosomes are replicated at each cell division. When they have shrunk to a particular critical length, this is the signal for the cell to enter the stage of senescence; if the cell ignores the warning, the telomeres are shortened further until finally the crisis occurs: when telomeres are extremely short, chromosomes are linked together or fragment, and the induced genetic chaos is lethal for the cell.

The aging or senescence process in normal cells, i.e. the loss of the ability to divide, to which normal cells are subject, is thus dependent on chromosomes in normal mortal cells losing about 50 to 200 DNA nucleotides at their telomeric ends at each cell division. Loss of these terminal nucleotides (telomeres) has the function of a type of mitotic clock which records the number of cell divisions. Retention of telomeres appears to be necessary for cells to escape the senescence process and be able to divide indefinitely.

The protective mechanism described above is inactivated during the course of degeneration in most cancer and tumor cells, specifically by activation of a gene which contains the instructions for synthesizing an enzyme called telomerase. This enzyme systematically replenishes the telomere sections which are otherwise shortened, and thus permanently maintains them and makes the cell able to divide further virtually without limit. Thus, in most neoplastic and cancerous diseases, the immortality of the cells results from the retention of short but stable telomeres owing to the action of telomerase. The resulting potential immortality of the cells is unfavorable in several ways: firstly, it contributes to the possibility of a tumor becoming very large, and secondly it gives precancerous or already genuine cancer cells time to accumulate further mutations which increase their abilities to proliferate, to penetrate into other tissues and finally to metastasize.

It has been found that the unlimited cell growth of degenerate cells is based in about 80% of all neoplastic diseases on impaired regulation of telomerase. The treatment of neoplastic or cancerous diseases via telomerase inhibitors therefore appears to make a promising therapy possible for these diseases. Consequently, many attempts have already been made in the art to develop active ingredients for inhibiting telomerase.

Thus, for example, WO 00/74667 A2 proposes the use of telomerase inhibitors (e.g. AZT) in combination with an active ingredient which induces telomere destruction (e.g. paclitaxel) for cancer treatment. WO 99/65875 A1 and U.S. Pat. No. 5,863,936 propose the use of specific heterobicyclic systems as telomerase inhibitors for the therapy of cancerous diseases. Catechol derivatives like those described in European published specification EP 0 938 897 A1 are said likewise to be employable as telomerase inhibitors for cancer treatment.

Attempts are also made in the art to intervene by other mechanisms at the molecular or cellular level in the proliferation of tumor or cancer cells. Thus, neoplastic or cancerous diseases are treated in the state of the art by employing many alkylating agents which, via alkylation of the DNA, eventually induce direct damage of the DNA of the tumor or cancer cells (e.g. cyclophosphamide, ifosfamide, carmustine, chlorambucil, etc.). Likewise used for tumor or cancer therapy are substances which, via inhibition of topoisomerases, intervene in the replication of the tumor or cancer cells (e.g. camptoceticin, 9-aminocamptothecin, irinotecan, topotecan, doxorubicin, etc.) (cf., for example, Clive Page et al., Integrated Pharmacology, Mosby, 1997).

Whereas—besides alkylating active ingredients—there are some topoisomerase inhibitors in clinical use, at present no active ingredient is in clinical use for the treatment of various tumors which acts via inhibition of telomerase or combines the properties of inhibition of topoisomerase and of telomerase.

SUMMARY OF THE INVENTION

The object of the present invention is thus to find and provide active ingredients and medicaments which are suitable in particular for the treatment of neoplastic and cancerous diseases, but where appropriate also of other diseases (e.g. viral diseases).

DETAILED DESCRIPTION

Figure 1A:
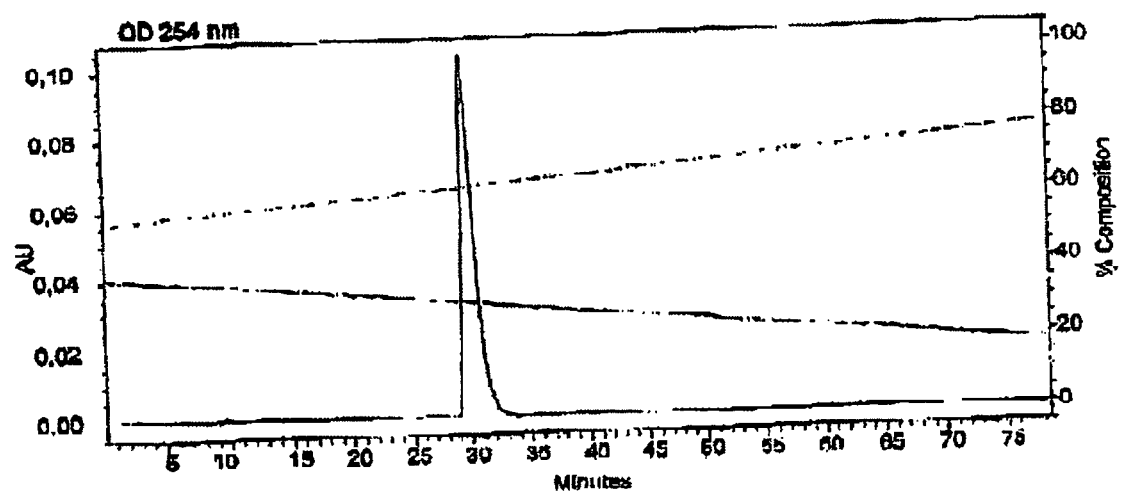
FIG. 1a shows a representative chromatogram of the substance (Ic') from the analytical RP-HPLC (purity test) at 254 nm, flow rate=1 ml/min, T=40° C., gradient system as indicated. The upper line corresponds to the concentration of inhibition of human telomerase obtained from cells of a colon carcinoma (HCT8 WT) by substance (Ic').

The applicant has now found, surprisingly, that substituted bicyclo[3.3.1]nonane-2,4,9-triones of the general formula (I)

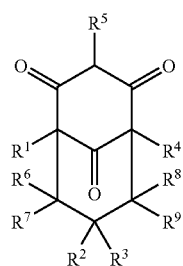

in which:

$R^1$, $R^2$, $R^4$ and $R^5$, identical or different, are independently of one another one of the following groups:

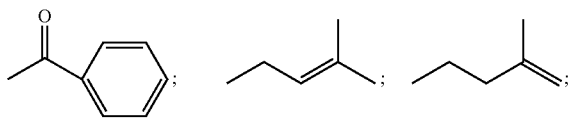

-continued

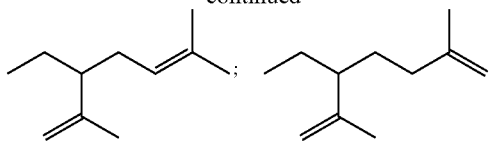

but with the proviso that if one of the radicals $R^1$ or $R^2$ or $R^4$ or $R^5$ is a benzoyl group, none of the other of these radicals is a benzoyl group;

$R^3$ is a hydrogen atom;

$R^6$ and $R^7$ are both in each case a methyl group or else in each case a hydrogen atom, and $R^8$ and $R^9$ are both in each case a methyl group or else in each case a hydrogen atom, but with the proviso that if $R^6$ and $R^7$ are methyl groups, $R^8$ and $R^9$ are hydrogen atoms, and that if $R^8$ and $R^9$ are methyl groups, $R^6$ and $R^7$ are hydrogen atoms;

and their physiologically tolerated salts, hydrates, isomers, in particular stereoisomers, tautomers and structural isomers, derivatives, prodrugs and metabolites are particularly suitable for the prophylactic and/or therapeutic (curative) treatment of neoplastic and cancerous diseases.

The present invention thus firstly relates to the use of the aforementioned compounds of the general formula (I), including their physiologically tolerated salts, hydrates, isomers, in particular stereoisomers, tautomers and structural isomers, derivatives, prodrugs and metabolites for producing medicaments for the prophylactic and/or therapeutic treatment of neoplastic and/or cancerous diseases, specifically of humans and of animals, i.e. both in the human and the veterinary medical sector.

Physiologically tolerated or acceptable salts of the compounds of the general formula (I) may be for example salts with mineral acids, carboxylic acids or sulfonic acids; particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid. However, salts with conventional bases may also be mentioned as physiologically tolerated or acceptable salts, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methyl-morpholine, dihydroabiethylamine, 1-ephenamine or methylpiperidine.

The present invention also includes the hydrates of the compounds of the general formula (I). The forms of the compounds of the above general formula (I) which are referred to as hydrates according to the invention are those which, in the solid or liquid state, form a molecular compound (hydrate) by hydration with water. In hydrates, the water molecules are attached by intermolecular forces, in particular hydrogen bonds. Solid hydrates contain water as so-called water of crystallization in stoichiometric or non-stoichiometric ratios, and the water molecules need not be equivalent in relation to their binding state. Examples of hydrates are sesquihydrates, monohydrates, dihydrates, trihydrates, etc. Equally suitable according to the invention are also the hydrates of salts of compounds of the general formula (I).

The present invention also includes the isomers of the compounds of the general formula (I). The concept of isomers for the purposes of the present invention is used as comprehensive designation of all possible forms of isomerism. Nonrestrictive examples of isomers included by the present invention are, in particular, stereoisomers, tautomers and structural isomers.

Thus, the compounds of the general formula (I) may, depending on the substitution pattern, occur in isomeric forms, in particular as stereoisomers, e.g. either as stereoisomers which are related as image and mirror image (enantiomers) or else as stereoisomers which are not related as image and mirror image (diastereomers). The present invention includes all stereoisomeric forms of the compounds of the general formula (I), i.e. both the enantiomers and the diastereomers as well as respective mixtures thereof. The enantiomeric forms can, just like the diastereomers, be separated in a manner known per se into stereoisomerically uniform constituents.

The compounds of the general formula (I) may also exist in tautomeric forms. This is known to the skilled worker, and such compounds are likewise included within the scope of the present invention. Examples of tautomeric forms are, for example, the following keto-enol tautomers:

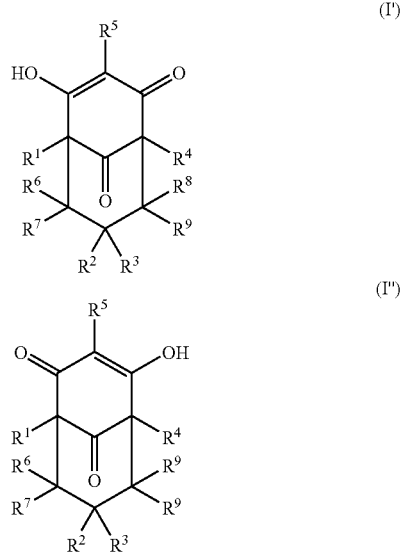

If $R^5$ is, for example, a benzoyl group, a further type of keto-enol tautomerism is possible.

The compounds of the general formula (I) may additionally exist as structural isomers, in particular positional isomers (substitution isomers). This is known to the skilled worker, and such compounds are likewise included within the scope of the present invention.

The present invention also includes derivatives of the compounds of the general formula (I) (e.g. ethers such as alkyl ethers, such as, for example, methyl ethers, which can be obtained for example by alkylation of the tautomeric forms (I') and (I")). Derivatives of the compounds of the general formula (I) which are particularly preferred according to the invention are the pegylated derivatives, especially the polyalkylene glycol ethers, preferably polyethylene glycol ethers (PEG ethers), of the tautomeric forms (I') and (I"). In addition, chemical modifications are also possible, in particular in relation to the substituents $R^1$ to $R^9$ (e.g. by side-group derivatization).

The present invention equally also includes prodrugs and metabolites of the compounds of the general formula (I). The forms of the compounds of the above general formula (I) which are referred to according to the invention as prodrugs are those which themselves may be biologically active or inactive but can be converted into the appropriate biologically active form (for example by metabolism, solvolysis or in other ways). The products of the compounds of the general formula (I) referred to as metabolites according to the invention are in particular those resulting from metabolism or transformed in metabolism.

The compounds of the general formula (I) are natural products and can be obtained for example by chromatographic removal from the propolis extract of Caribbean bees. Propolis is a dark yellowish to pale brown, resinous mass which softens between the fingers and has a spicy-balsamic odor and which is collected by bees in particular from the buds of flowers and is used in the hive as coating of the walls and for strengthening the combs. Propolis has a very complicated chemical structure and its exact composition depends on the local flora in each case. Propolis contains more than 200 different chemical substances, including relatively large proportions of waxes and resins, essential and aromatic oils, and a large number of other chemical substances, including for example flavonoids, caffeic acid derivatives and, in the case of Caribbean propolis, also the compounds of the general formula (I).

The compounds of the general formula (I) can also be isolated directly from the plant sap or resin (e.g. from the resin, the latex, the leaves, the flower, etc.) of various *Clusia* species, family of clusiaceae or guttiferae (e.g. from *Clusia grandiflora, Clusia rosea* or *Clusia renggerioides*):

Thus, A. J. Marsaioli et al. "The Ecosystem of Microorganisms, Bees, and *Clusia* Floral Resin and Oils, from the Chemistry Point of View", Pure Appl. Chem., Volume 70, 11, pages 2116 ff. (1998), C. M. A. de Oliveira et al. "Two polyisoprenylated benzophenones from the floral resins of three *Clusia* species", Phytochemistry 50 (1999), pages 1073–1079 and A. L. M. Porto et al. "Polyisopenylated benzophenones from *Clusia* floral resins", Phytochemistry 55 (2000), pages 755–768, describe the isolation of various clusianone derivatives of the above general formula (I) starting from the resins or constituents of various plants of the species *Clusia* (family of clusiaceae or guttiferae) by chromatographic methods (reaction of the resins with diazomethane in diethyl ether and subsequent column chromatography on a column packed with silica gel with hexane/ethyl acetate or hexane/diethyl ether as eluent (gradient column), followed by preparative thin-layer chromatography on silica gel/silver nitrate with benzene/ethyl acetate as eluent).

Isolation of clusianone itself starting from the resin of plants of the family of clusiaceae or guttiferae, namely *Clusia congestiflora*, and its structural elucidation is described by L. E. McCandlish et al. "The Structures of Two Derivatives of Bicyclo[3.3.1]nonane-2,4,9-trione. A Natural Product: Clusianone, $C_{33}H_{42}O_4$, and Trimethylated Catechinic Acid, $C_{18}H_{20}O_6$" in Acta Cryst. (1976), B32, pages 1793–1801.

M. H. Santos et al. "Efeito de constituintes químicos extraídos do fruto de Rheedia gardneriana (bacuparí) sobre bactérias patogênicas" in Brazilian Journal of Pharmaceutical Sciences (Revista Brasileira de Ciências Farmacêuticas), Volume 35, No. 2, July/December 1999, pages 297–301 and "Epiclusianon: A New Natural Product Derivative of Bicyclo-[3.3.1]nonane-2,4,9-trione" Acta Cryst. (1998), C54, pages 1990–1992, describe the isolation of epiclusianone from the flower extract of *Rheedia gardneriana* (bacuparí), a plant of the family of clusiaceae.

F. delle Monache et al. "Prenylated Benzophenones From *Clusia Sandiensis*", Phytochemistry, Volume 30, No. 6, pages 2003–2005 (1991) describe the isolation of various clusianone derivatives starting from the plant resin of *Clusia Sandiensis* by means of chromatographic methods (column chromatography followed by preparative thin-layer chromatography).

The entire disclosure content of the aforementioned documents of the prior art relating to the preparation and isolation of the compounds of the general formula (I) is hereby incorporated by reference.

The applicant has now found, entirely surprisingly, that the compounds of the general formula (I) including their physiologically tolerated salts, hydrates, isomers, in particular stereoisomers, tautomers and structural isomers, derivatives, prodrugs and metabolites show a valuable range of pharmacological effects which could not have been predicted and are therefore suitable for the prophylaxis and/or treatments of diseases, in particular cancerous and neoplastic diseases of every type, but also of viral diseases of every type.

The compounds of the general formula (I) including their physiologically tolerated salts, hydrates, isomers, in particular stereoisomers, tautomers and structural isomers, derivatives, prodrugs and metabolites can accordingly preferably be employed in medicaments for the prophylaxis and/or treatment of diseases, preferably of neoplastic and cancerous diseases (cytostatics) and of viral diseases (antiviral compositions or virustatics). The present invention thus further relates also to pharmaceutical compositions or medicaments, in particular cytostatics or antiviral compositions (virustatics), which comprise at least one compound of the general formula (I) as defined above and/or its physiologically tolerated salts, hydrates, isomers, in particular stereoisomers, tautomers and structural isomers, derivatives, prodrugs and metabolites, preferably in therapeutically effective amounts, together with a pharmaceutically acceptable, essentially non-toxic carrier or excipient.

The applicant has surprisingly found that the compounds of the general formula (I) act inter alia as topoisomerase inhibitors, in particular as inhibitors of topoisomerase I. In addition, they generally also show a telomerase-inhibitory effect. Ultimately, the compounds of the general formula (I) employed according to the invention induce destruction of the DNA in tumor and cancer cells.

The topoisomerase-inhibitory and telomerase-inhibitory effect of the compounds of the general formula (I) used according to the invention is distinctly higher than for the compounds known in the art. Thus, for example, the compounds of the general formula (I) show in in vitro tests a considerably stronger inhibition of topoisomerase I than conventional therapeutic agents (e.g. topotecan). In addition, the compounds of the general formula (I) also act as regulators within MAP kinase signal transduction.

The fact that the compounds of the general formula (I) combine the properties of inhibition of topoisomerase and telomerase explains their valuable properties and their particular suitability in relation to their use for the prophylactic and therapeutic (curative) treatment of neoplastic and cancerous diseases of every type (primary tumors, metastases, precanceroses or preliminary stages of cancer, benign and malignant tumors, etc.). By contrast, no active ingredient and no product is known in the art which combines the properties of inhibition of topoisomerase on the one hand and telomerase on the other hand in a single molecule.

The active ingredients of the general formula (I) used according to the invention show not only an antitumor effect but additionally also an antimetastatic effect.

The active ingredients of the general formula (I) used according to the invention surprisingly show an unexpectedly good cytostatic effect even on carcinomas which display defined resistances to established chemotherapeutic agents. In addition, no resistances to the active ingredients of the general formula (I) have been observed. Moreover, the active ingredients of the general formula (I) used according to the invention have the advantage that they show no cross-resistances with already established medicaments or chemotherapeutic agents.

Diseases which may be mentioned as non-restrictive examples of neoplastic and cancerous diseases for whose treatment the compounds of the general formula (I) can be employed are the following: intestinal cancer (carcinomas of the colon), breast cancer (carcinomas of the breast), ovarian carcinomas, uterine carcinomas, lung cancer, stomach cancer, liver cancer, carcinomas of the pancreas, renal cancer, bladder cancer, prostate cancer, testicular cancer, bone cancer, skin cancer, Kaposi sarcomas, brain tumors, myosarcomas, neuroblastomas (e.g. retinoblastomas), lymphomas and leukemias.

It is preferred according to the invention to use the following compounds of the formulae (Ia), (Ib), (Ic) and (Id) including their physiologically tolerated salts, hydrates, isomers, in particular stereoisomers, tautomers and structural isomers, derivatives, prodrugs and metabolites:

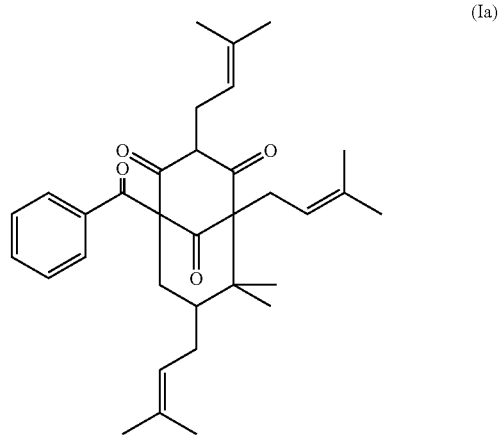

(Ia)

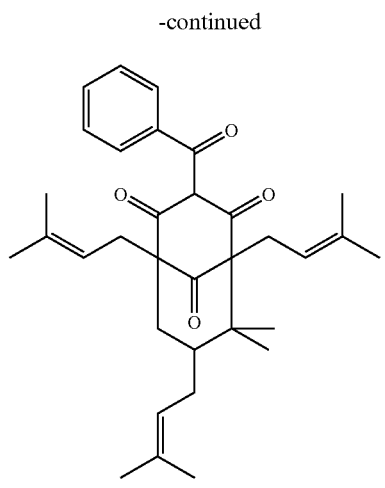
(Ib)

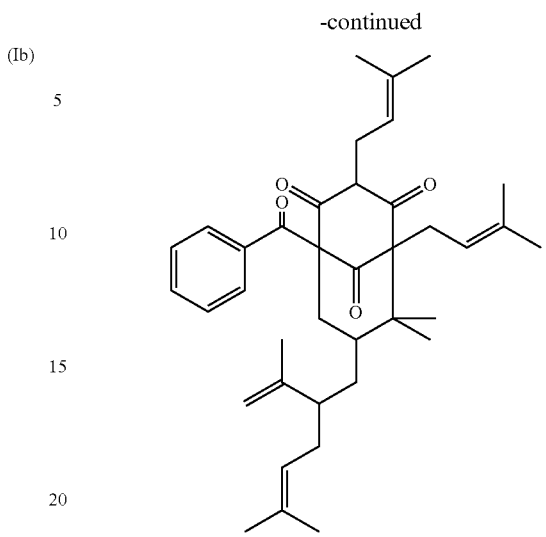
(Id)

It is particularly preferred according to the invention to use the following compound of the general formula (Ic) including its physiologically acceptable salts, hydrates, isomers, in particular stereoisomers, tautomers and structural isomers, derivatives, prodrugs and metabolites:

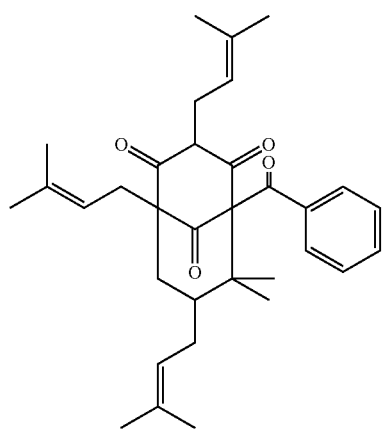
(Ic)

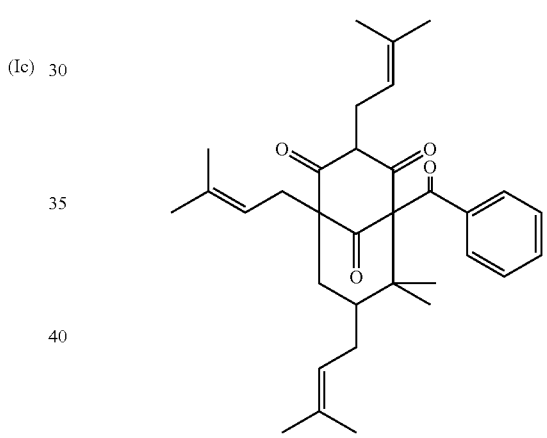
(Ic)

The compound of the general formula (Ic) is one of a plurality of keto/enol tautomers which exist in equilibrium with one another:

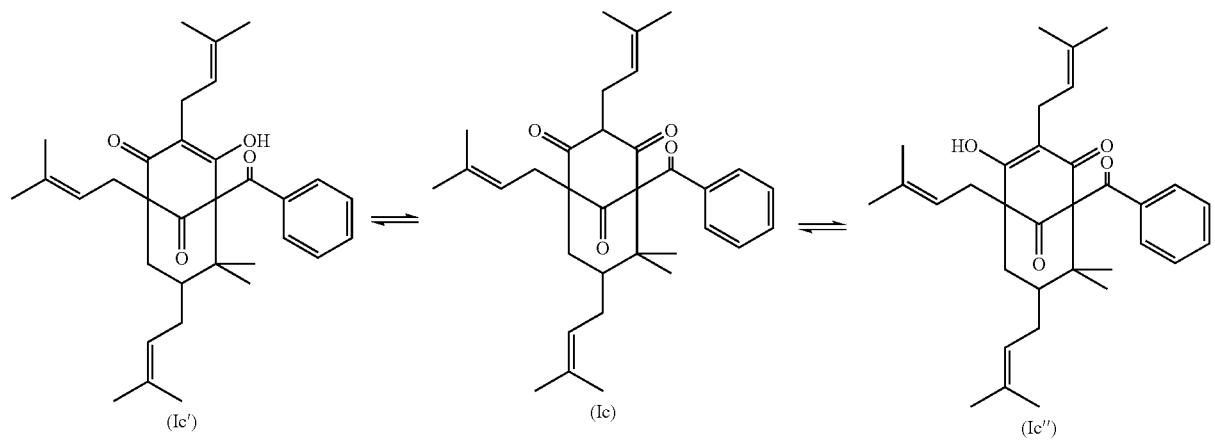

It is very particularly preferred according to the invention for the compound of the general formula (Ic) to have the following configuration.

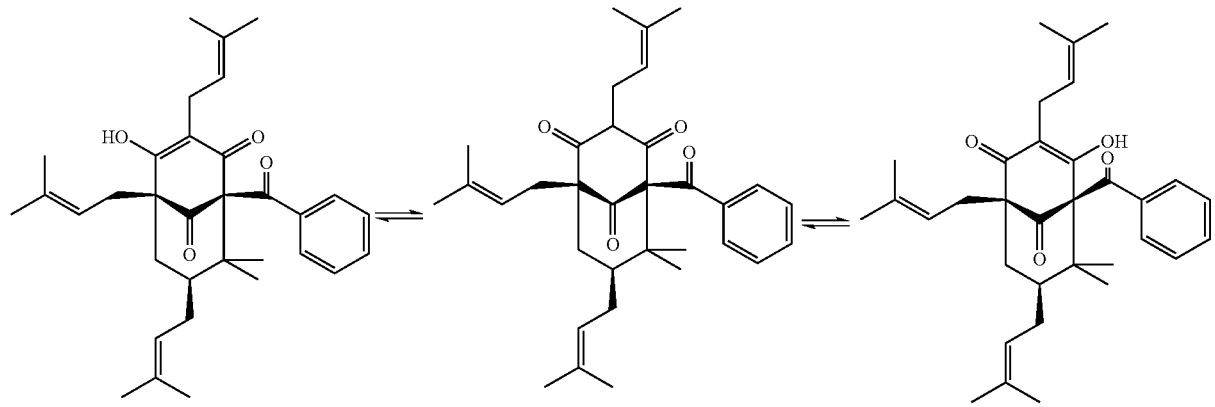

The applicant has additionally found that it may in certain cases be advantageous to employ or to administer the compounds of the general formula (I) and/or their physiologically tolerated salts, hydrates, isomers, in particular stereoisomers, tautomers and structural isomers, derivatives, prodrugs and metabolites in combination with at least one further chemotherapeutic agent, in particular a protein kinase inhibitor, preferably an MAP kinase inhibitor. Particularly good results in the therapy of cancerous and neoplastic diseases can be achieved with a combination of compounds of the general formula (I) and/or their physiologically tolerated salts, hydrates, isomers, in particular stereoisomers, tautomers and structural isomers, derivatives, prodrugs and metabolites on the one hand and a protein kinase inhibitor, preferably MAP kinase inhibitor, on the other hand. Such combinations surprisingly have synergistic effects.

The present invention thus also relates to a pharmaceutical combination, in particular cytostatic combination, which includes (A) at least one compound of the general formula (I) as defined above, and/or its physiologically tolerated salts, hydrates, isomers, in particular stereoisomers, tautomers and structural isomers, derivatives, prodrugs and metabolites; and (B) at least one further chemotherapeutic agent, in particular a protein kinase inhibitor, preferably MAP kinase inhibitor.

The individual components (A) and (B) of the combination of the invention can be used or administered either simultaneously or else sequentially. The pharmaceutical combination may include components (A) and (B) either as functional unit, in particular in the form of a mixture, of a mix or of a blend, or else (spatially) separate from one another.

Protein kinase inhibitors have, as their name indicates, inhibitory effects in relation to the activity of protein kinases, i.e. enzymes which transfer the γ-phosphate groups from ATP to tyrosine or serine and threonine side chains. Suitable for the pharmaceutical combination of the invention and the combination therapy of the invention in particular of neoplastic and cancerous diseases are protein kinase inhibitors of every type, e.g. all protein kinase inhibitors known in the art (e.g. certain low molecular weight heterocyclic inhibitors such as staurosporine, 2'-amino-3'-methoxyflavone, 1,4-diamino-2,3-dicyano-1,4-[2-aminophenylthio] butadiene, SB 203580 from SmithKline Beecham, etc.). A synergistic effect may be observed in these cases.

It is particularly preferred to use MAP kinase inhibitors for the pharmaceutical combination of the invention and the combination therapy of the invention of neoplastic and cancerous diseases. MAP kinase inhibitors have, as their name indicates, inhibitory effects in relation to the activity of MAP kinases (MAP=mitogen activated protein), i.e. enzymes which are active in particular during mitosis and which transfer terminal phosphate residues from nucleotide triphosphates to appropriate substrates. In this way, MAP kinase inhibitors prevent mitosis and thus cell division of cancer and tumor cells. Suitable for the pharmaceutical combination of the invention and the combination therapy of the invention in particular of neoplastic and cancerous diseases are MAP kinase inhibitors of every type, e.g. all MAP kinase inhibitors known in the art. Examples of MAP kinase inhibitors which can be employed according to the invention are mentioned for example in the following publications, the entire contents of which are hereby incorporated by reference: WO 99/32111 A, WO 99/64400 A, WO 98/52941 A, WO 98/52937 A, WO 97/44467 A, WO 98/27098 A, WO 98/52558 A, WO 98/52940 A, WO 99/32110 A, WO 99/32463 A, WO 99/58502 A, WO 99/58523 A and WO 99/00357 A.

The applicant has additionally found, surprisingly, that the aforementioned compounds of the general formula (I) also show a regulatory activity within MAP kinase signal transduction, i.e. act as regulators within MAP kinase signal transduction.

The compounds of the general formula (I) are additionally also suitable for the treatment of viral diseases and as pharmaceutically active ingredients of antiviral compositions (virustatics) (e.g. for the treatment of herpetic diseases or HIV). The present invention thus also relates to the use of compounds of the general formula (I), as defined above, and of their physiologically tolerated salts, hydrates, isomers, in particular stereoisomers, tautomers and structural isomers, derivatives, prodrugs and metabolites for the prophylactic and/or therapeutic (curative) treatment of viral diseases of every type.

The present invention additionally relates also to a method for the prophylaxis and/or treatment of diseases of the human or animal body, in particular neoplastic and cancerous diseases or viral diseases of every type, using the compounds of the general formula (I) including their physiologically tolerated salts, hydrates, isomers, in particular stereoisomers, tautomers and structural isomers, derivatives, prodrugs and metabolites in therapeutically effective doses, where appropriate also in combination with further active ingredients, in particular chemotherapeutic agents (e.g. protein kinase inhibitors such as, for example, MAP kinase inhibitors).

The active ingredients or active ingredient combinations employed according to the invention may, depending on the nature of the diseases to be treated, be administered systemically or else topically, in particular locally.

Suitable for administration of the active ingredients or active ingredient combinations employed according to the invention are all conventional administration forms. Examples of possible administration are oral, lingual, sublingual, buccal, rectal or parenteral (i.e. avoiding the intestinal tract, that is to say intravenous, intraarterial, intracardiac, intracutaneous, subcutaneous, transdermal, intraperitoneal or intramuscular), and oral and intravenous administration are particularly suitable; oral administration is very particularly preferred. Topical use is also possible (e.g. for the treatment of melanomas).

For the use according to the invention, the active ingredients or active ingredient combinations are converted in a known manner into conventional formulations such as, for example, uncoated tablets, coated tablets, pills, granules, aerosols, syrups, emulsions, suspensions, solutions, ointments, creams and gels of every type, in particular using inert, essentially non-toxic, pharmaceutically suitable carriers or solvents. It is additionally possible to introduce the active ingredients or active ingredient combinations employed as it were into liposomal "packages", i.e. as it were embedded or encapsulated in liposomes, which may in turn optionally be modified further (e.g. esterified with PEG). In this connection, the active ingredients or active ingredient combinations employed according to the invention can in each case be present in a therapeutically effective concentration, in particular in concentrations from about 0.0001 to about 99% by weight, preferably about 0.01 to about 95% by weight, of the complete mixture, i.e. in amounts sufficient to achieve the indicated or desired dosage range. It may nevertheless be necessary where appropriate to deviate from the aforementioned amounts, in particular as a function of the body weight or of the type of administration route, of the individual response to the medicament, of the type of formulation and of the time or interval over which administration takes place. Thus, it may in some cases be sufficient to make do with less than the aforementioned minimum amount, whereas in other cases said upper limit must be exceeded. Where larger amounts are administered, it may be advisable to divide these into a plurality of single doses over a defined period, e.g. over the day.

The formulations are produced for example by extending the active ingredients or active ingredient combinations with solvents (e.g. oils such as castor oil) and/or carriers, where appropriate using emulsifiers and/or dispersants, it being possible to use, e.g. where water is used as diluent, where appropriate organic solvents as auxiliary solvents.

Depending on the mode of administration, it has proved advantageous to administer the active ingredients or active ingredient combinations employed according to the invention in amounts of about 0.0001 to about 500 mg/kg of body weight, in particular about 0.0001 to about 100 mg/kg, preferably 0.01 to 50 mg/kg, to achieve effective results. It may nevertheless be necessary where appropriate to deviate from the aforementioned amounts, in particular as a function of the body weight or of the type of administration route, of the individual response to the medicament, of the type of formulation and of the time or interval over which administration takes place. Thus, it may in some cases be sufficient to make do with less than the aforementioned minimum amount, whereas in other cases said upper limit must be exceeded. Where larger amounts are administered, it may be advisable to divide these over a defined period, e.g. over the day, in particular for example in a plurality of single doses or as continuous administration (e.g. continuous infusion). Use in chronic therapy (e.g. in tablet form) is equally possible.

Further refinements, modifications and variations of the present invention can be identified and implemented directly by the skilled worker on reading the description without leaving the scope of the present invention.

The present invention is illustrated by means of the following exemplary embodiments which, however, by no means restrict the present invention.

Exemplary Embodiments

1-Benzoyl-8,8-dimethyl-2-hydroxy-3,5,7-tris-(3-methyl-2-butenyl)bicyclo[3.3.1]non-2-ene-4,9-dione (Ic') from propolis extract of Caribbean bees

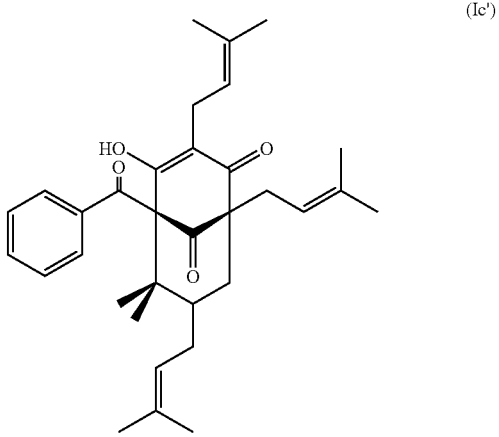

Isolation of the compound of the formula (Ic') and its physiological activity is described below.

The compound of the formula (Ic') exists in tautomeric equilibrium with the structures of the formulae (Ic) and (Ic"):

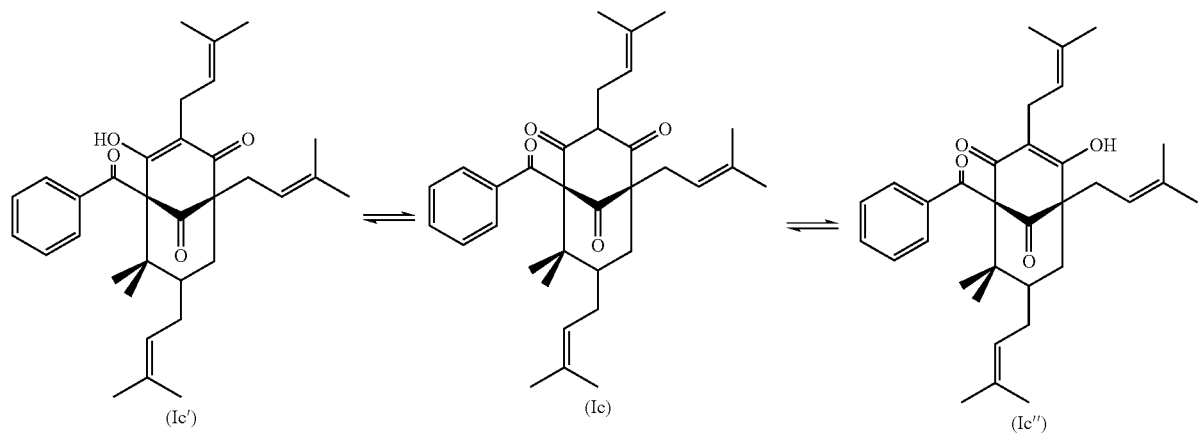

(Ic') (Ic) (Ic")

However, for the sake of simplicity, mention is made below only of the compound of the formula (Ic').

Preparation of Propolis Solutions

Propolis collected from beehives in the Caribbean is taken up in ethanol, and the insoluble waxes are removed by filtration. Defined volumes are dried, and the resulting powder is resuspended at a defined concentration in ethanol. The solutions are stored at room temperature with exclusion of light.

Semipreparative HPLC Fractionation of the Propolis Solutions

The fractionation takes place with an RP-HPLC system supplied by Waters GmbH (Eschborn) (Waters the Separator Module Alliance 2690, Waters PDA 996 Detektor, Waters Millennium Chromatography Manager). The fractionation is performed on a separation column supplied by Macherey-Nagel (Nucleosil 100-7 C18, 250×21 mm) using a gradient system at 40° C. (table 1). The aqueous phase consists of a 0.01 M ammonium formate solution (pH=7.00).

TABLE 1

| | | Gradient system | | |
|---|---|---|---|---|
| Time (min) | Flow rate (ml/min) | Ammonium formate % | Methanol % | Acetonitrile % |
| 0 | 4 | 50 | 30 | 20 |
| 80 | 4 | 10 | 70 | 20 |
| 180 | 4 | 0 | 80 | 20 |
| 190 | 4 | 0 | 80 | 20 |
| 200 | 4 | 50 | 30 | 20 |
| 210 | 4 | 50 | 30 | 20 |

The fractions each of 8 ml (2 min) obtained in this way are dried and resuspended in methanol and stored at room temperature with exclusion of light.

The cytotoxicity of the individual fractions is tested by diluting comparable volumes in a medium and investigating in the SRB assay described below. The target cell used is, inter alia, a bowel cancer cell line of human origin (HCT8 WT).

Purification of the Cytotoxic Fraction

The fraction with cytotoxic activity in the SRB assay is subjected to further purification. For this purpose, the gradient elution system is adapted to the polarity of the fraction to be purified. After renewed fractionation and testing of the fractions obtained by preparative RP-HPLC in the SRB assay it is possible to isolate a homogeneous substance (Ic'). The purity of the substance (IC') is demonstrated by means of UV spectroscopic data (FIG. 1b). A Waters Symmetry column packed with a modified C18 phase (250 mm×4.6 mm) is chosen as analytical separation column. The result is depicted in FIG. 1a.

Figure 1B:
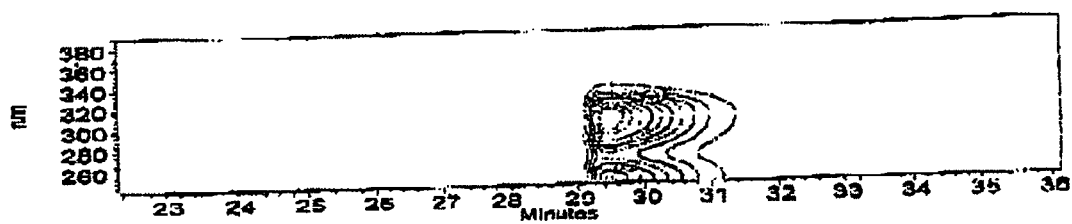

FIG. 1a shows a representative chromatogram of the substance (Ic') from the analytical RP-HPLC (purity test) at 254 nm, flow rate=1 ml/min, T=40° C., gradient system as indicated. The upper line corresponds to the concentration of methanol (%), the middle line to the concentration of aqueous phase (%, ammonium formate 0.01 M). The concentration of acetonitrile (%) is kept constant at 5% (lower line).

FIG. 1b shows the PDA data of the analysis shown in FIG. 1a. The substance (Ic') is obtained as homogeneous fraction. The UV spectrum under these elution conditions exhibits two maxima (254 and 308 nm).

Structure Elucidation

The initial isolation and characterization of the compound of the general formula (Ic') takes place without further derivatization (e.g. with diazomethane). The ethanolic extracts of propolis (collected in the Caribbean) can be purified as described previously by RP-HPLC analysis, by which means it is possible to provide the compound of the formula (Ic') for the first time in its non-derivatized form for further NMR spectroscopy investigations, in particular in sufficiently high purity (>98%; LC-MS; UV spectroscopic investigations by LC-PDA; MS).

For further confirmation of the structure, the compound of the formula (Ic') is converted by reaction with diazomethane into the corresponding methyl ethers. The O-methylated compounds are isolated (RP-HPLC) in the ratio 40/60.

The results of the NMR investigations ($^1$H-NMR, $^{13}$C-NMR, DEPT135, DEPT90, HMQC, HMBC, H,H—COSY90 (gs), 1D-NOE difference spectrum) are indicated in the following table:

DEPT stands for Distortionless Enhancement by Polarization Transfer.

COSY stands for COrrelated SpectroscopY. By this is generally meant $^1$H, $^1$H—COSY, which is also called the Jeener experiment after its "inventor" and represents the first 2D pulse sequence in the history of NMR.

HMQC stands for Heteronuclear Multiple Quantum Coherence.

HMBC stands for Heteronuclear Multiple Bond Correlation.
NOE stands for Nuclear Overhauser Effect.

Figure 1C:
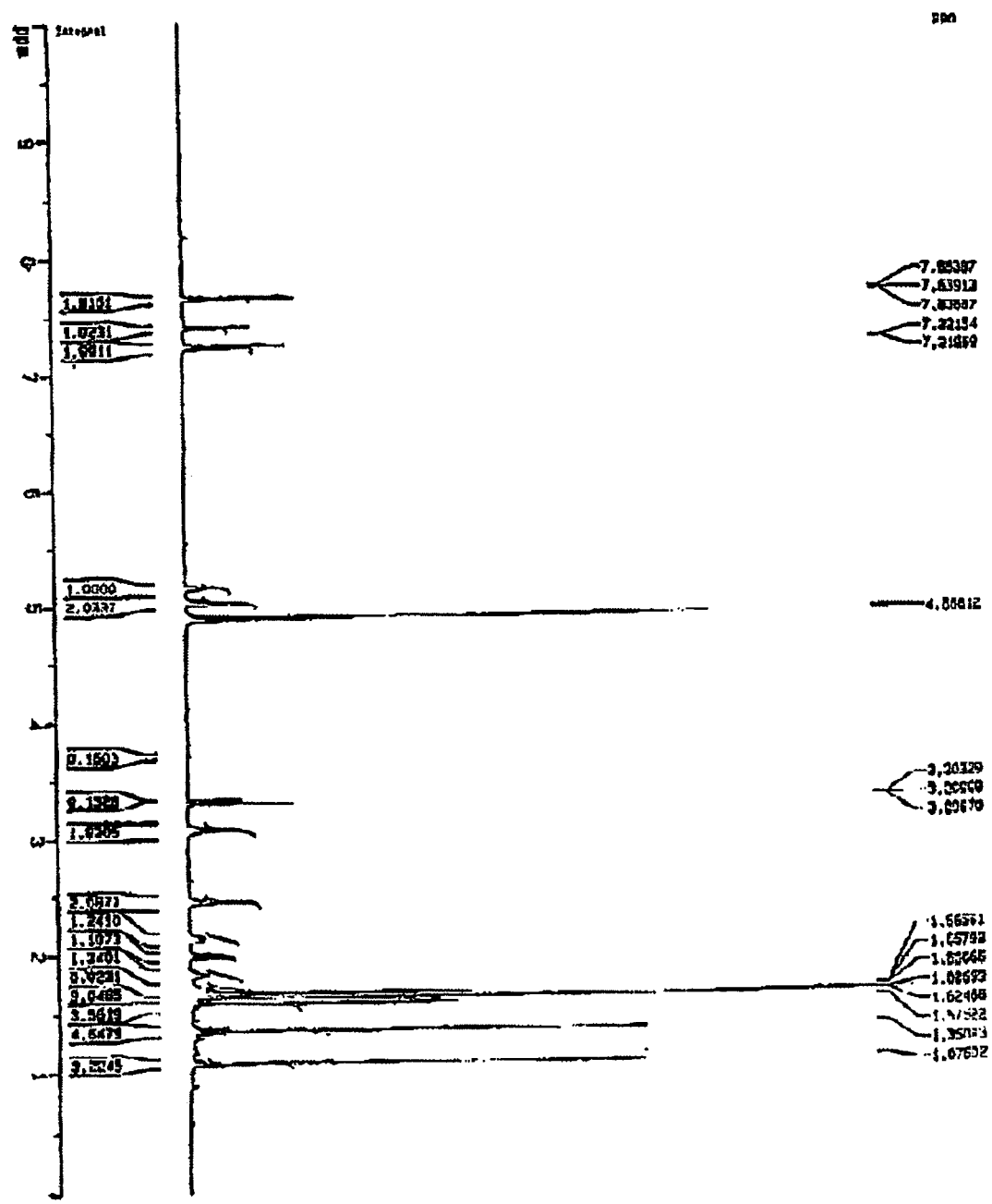
Figure 1D:
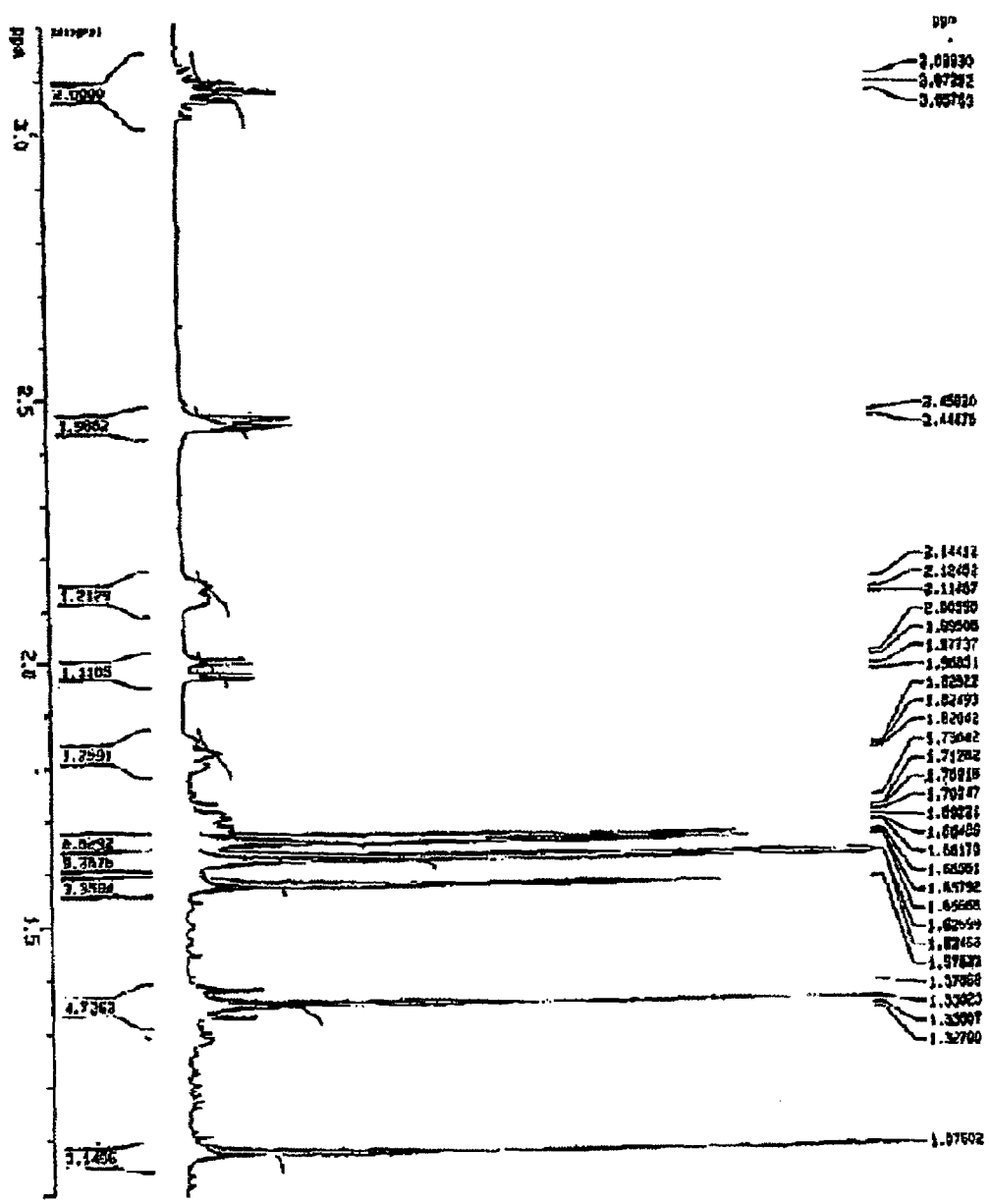
Figure 1E:
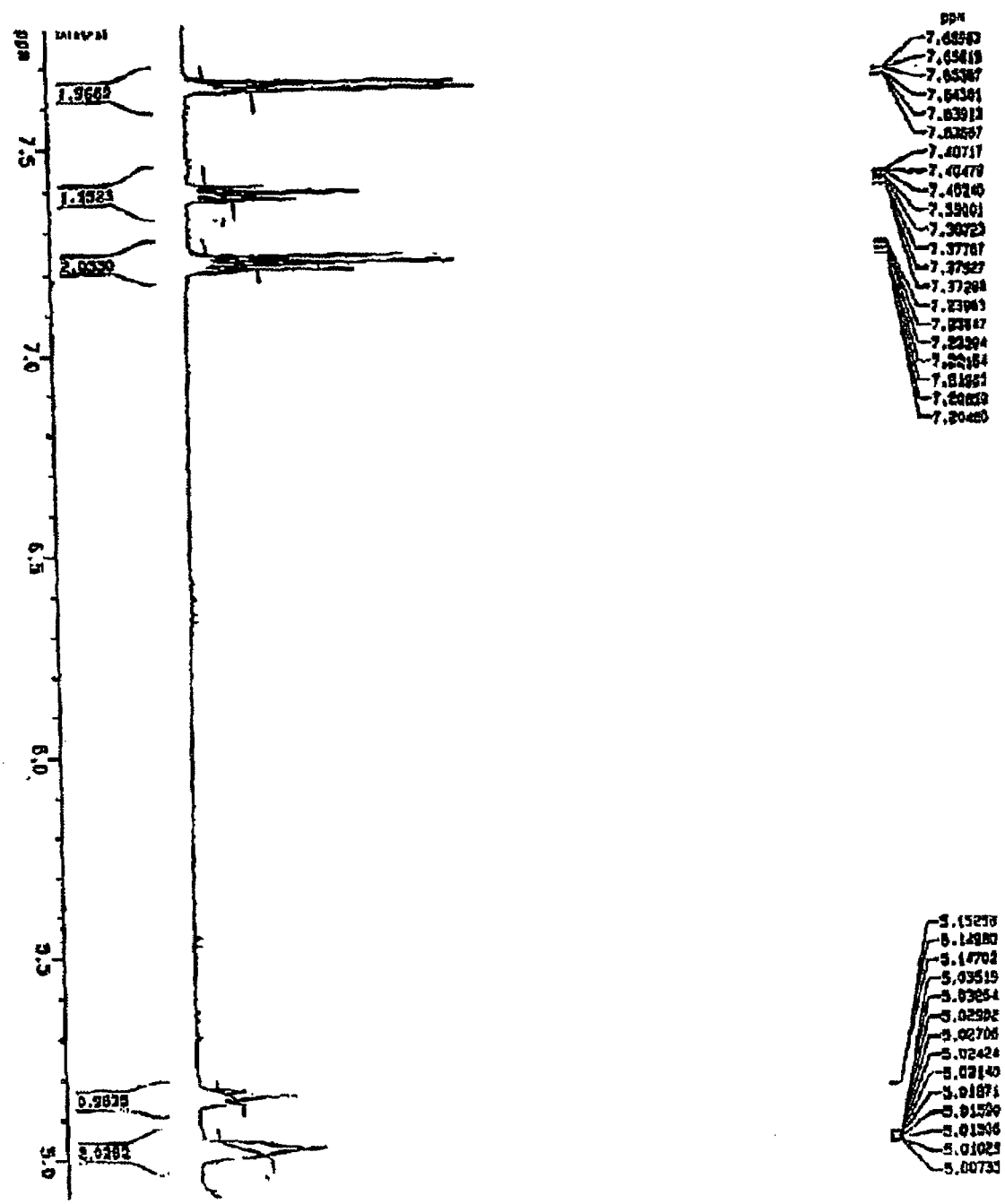

FIGS. 1c, 1d and 1e are $^1$H-NMR spectra of the compound (Ic') (measurement frequency: 500 MHz, solvent: $CD_3OD$).

Figure 1F:
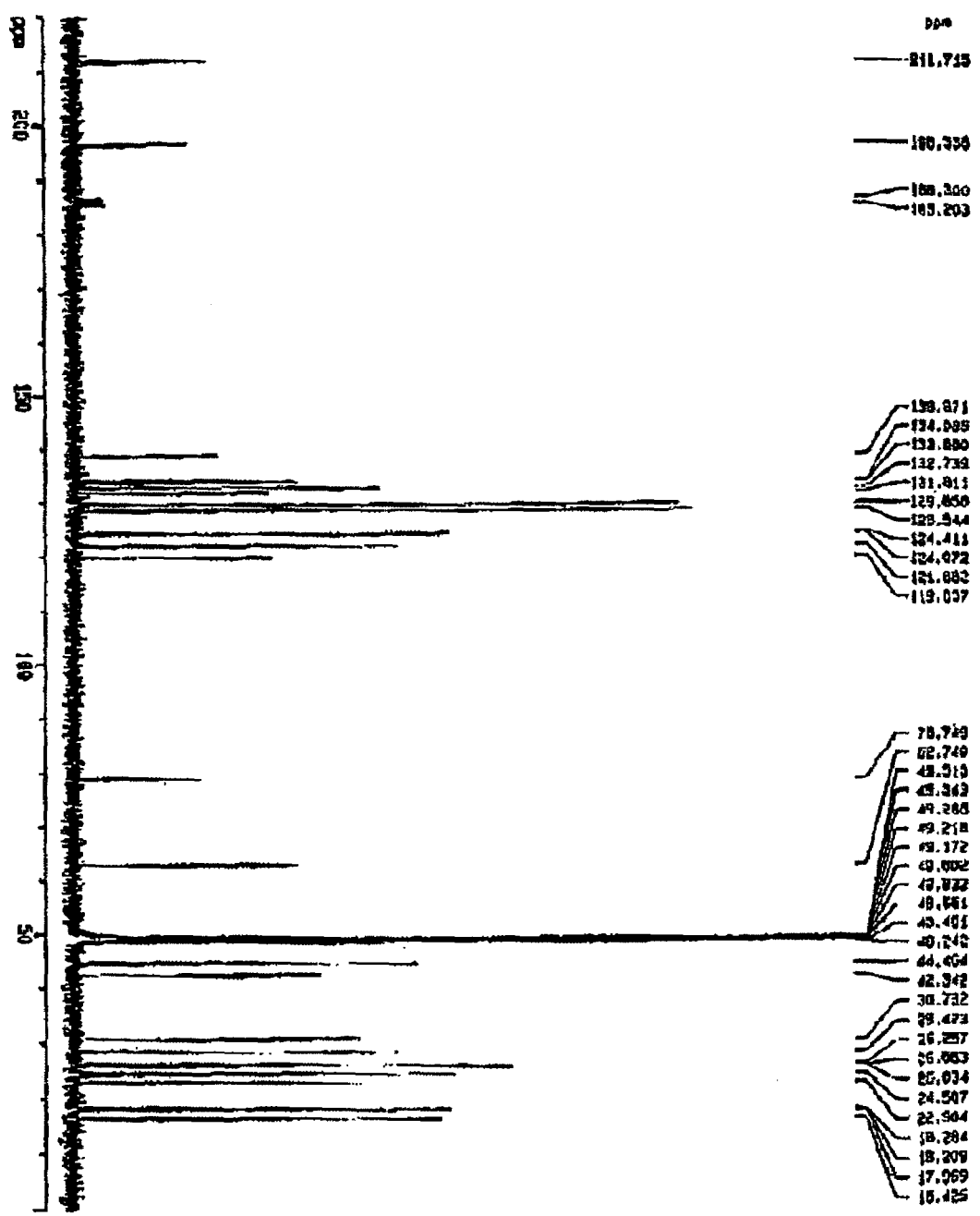

FIG. 1f depicts a $^{13}$C-NMR spectrum of the compound (Ic') (measurement frequency: 125 MHz, solvent: $CD_3OD$).

Figure 1G:
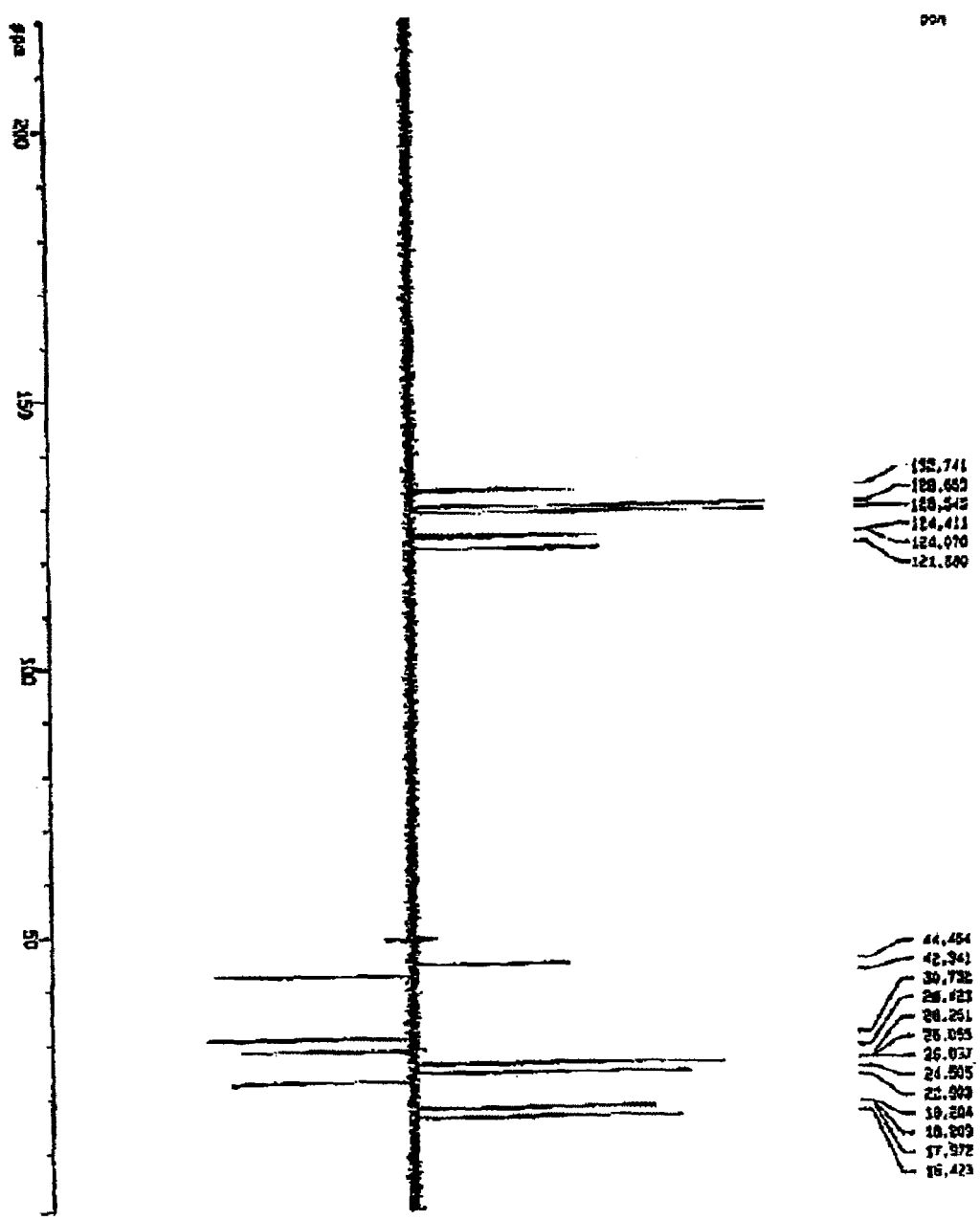
Figure 1H:
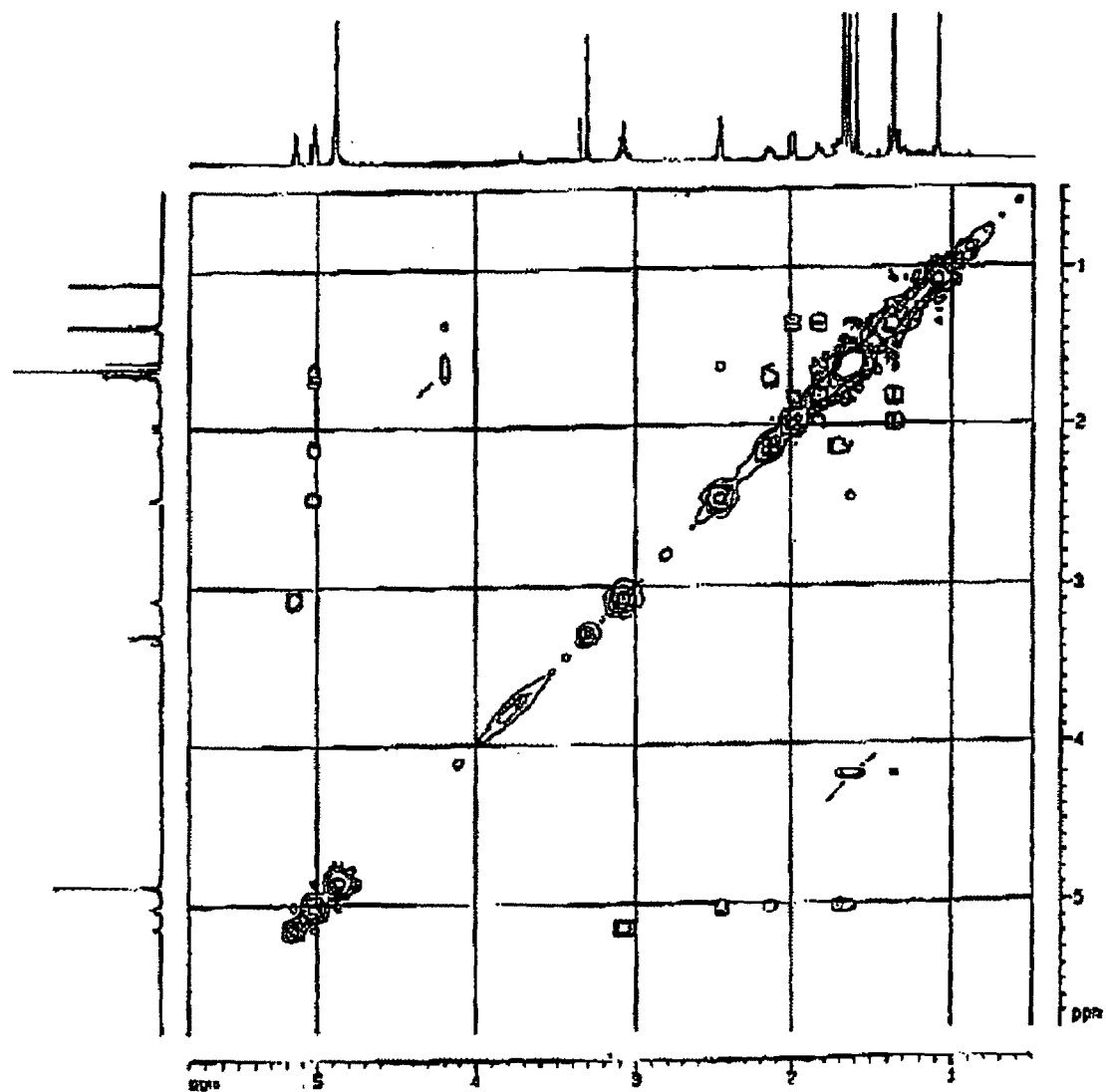
Figure 1I:
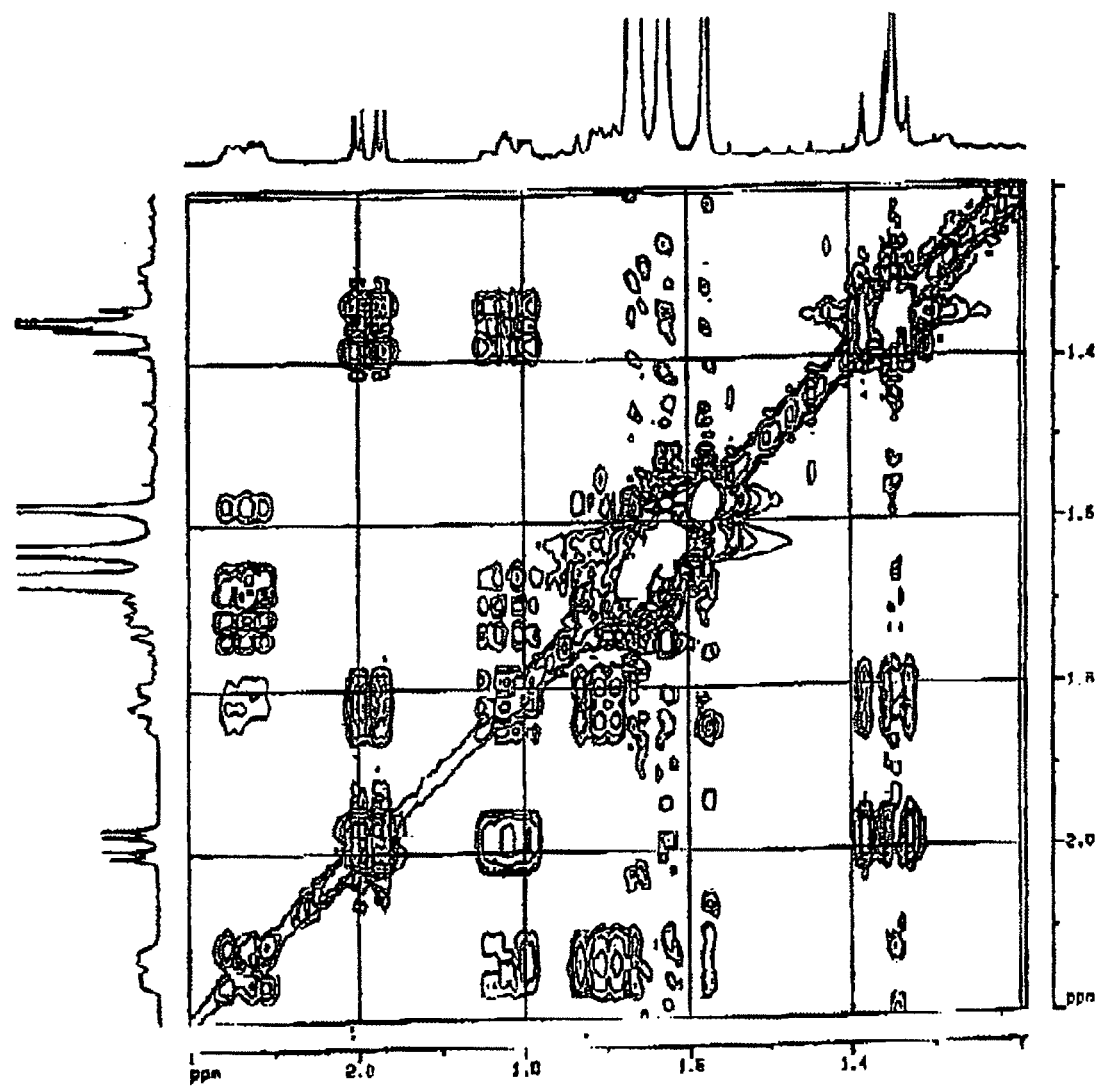
Figure 1J:
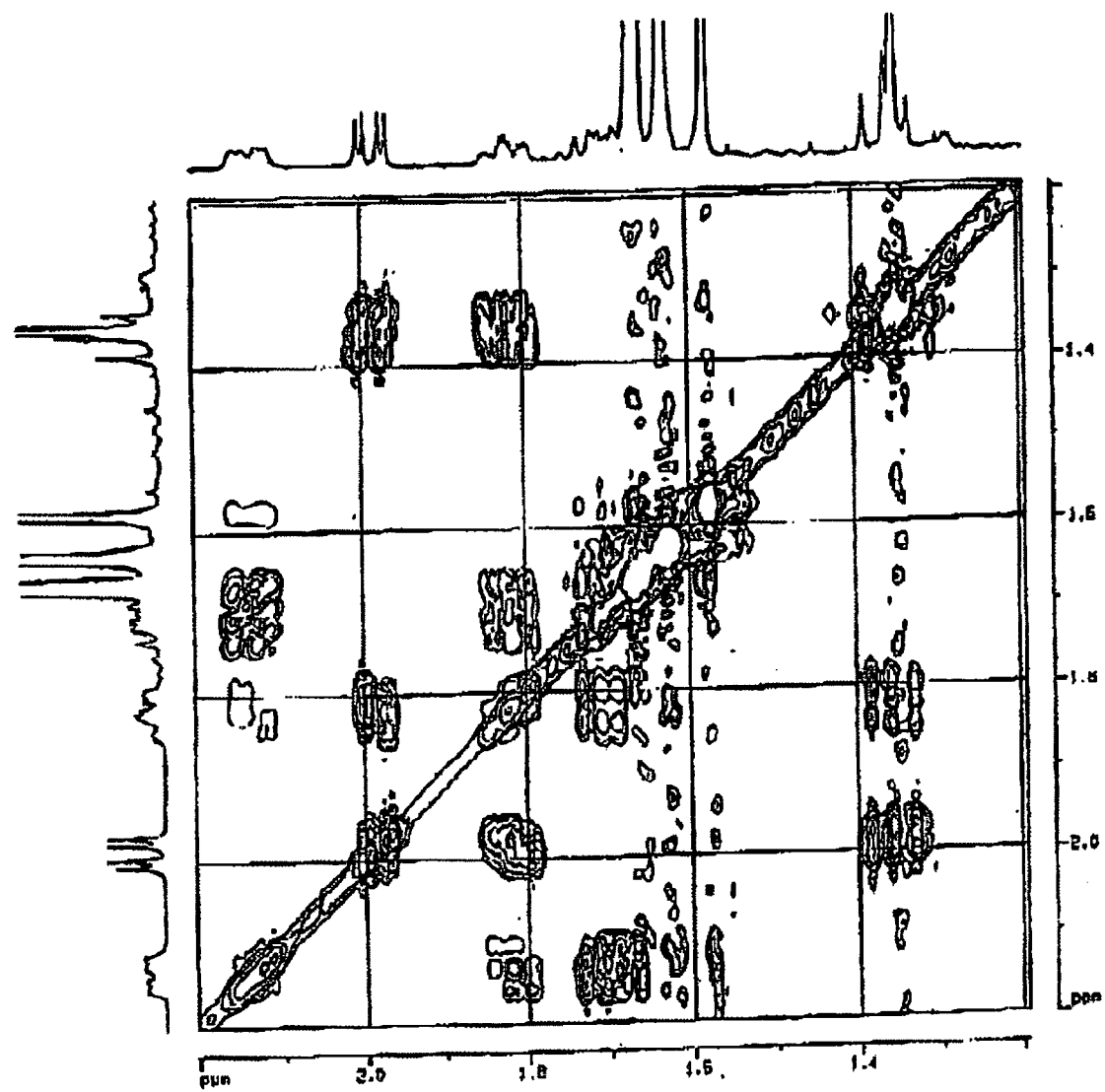
Figure 1K:
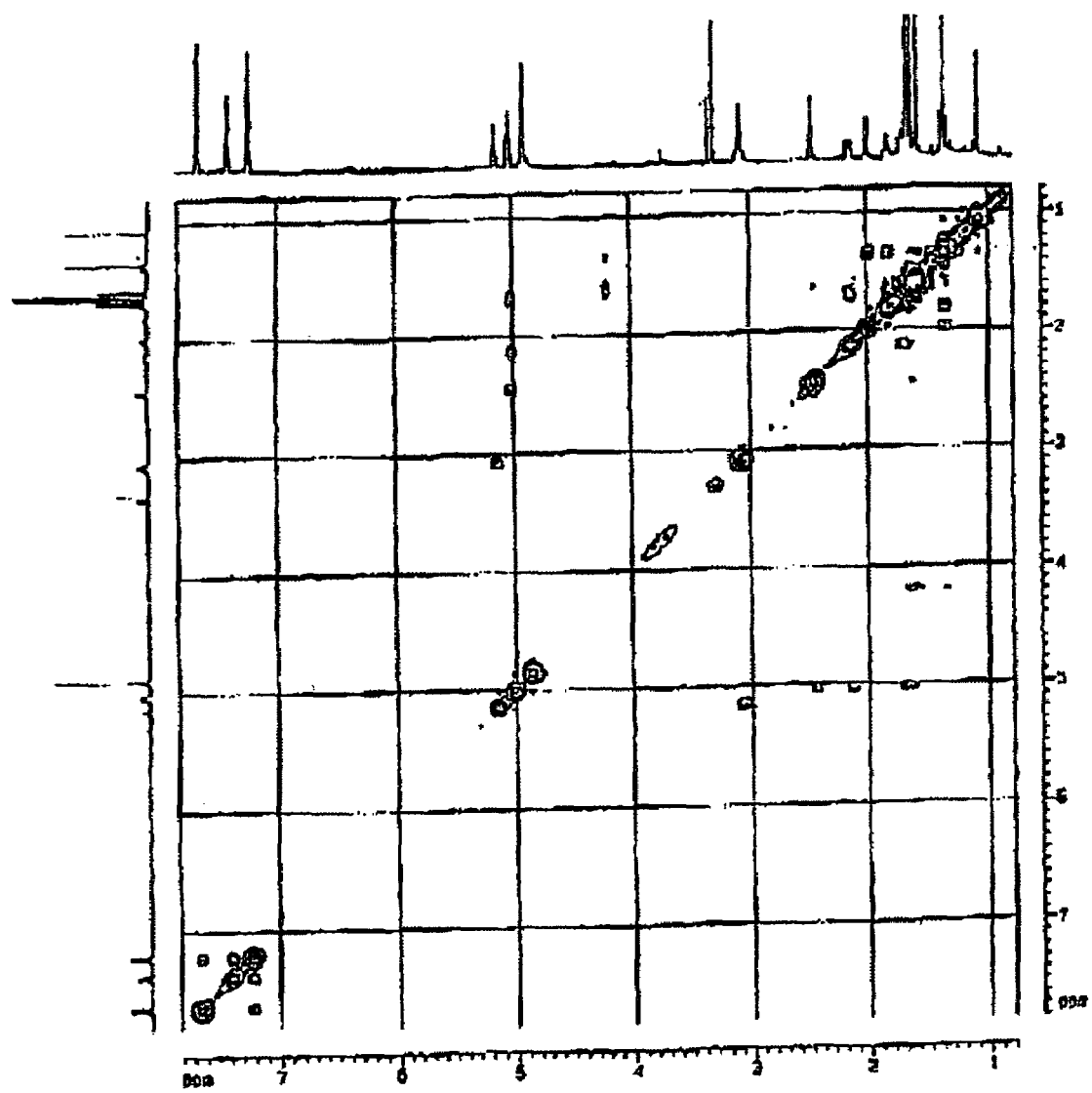
Figure 11:
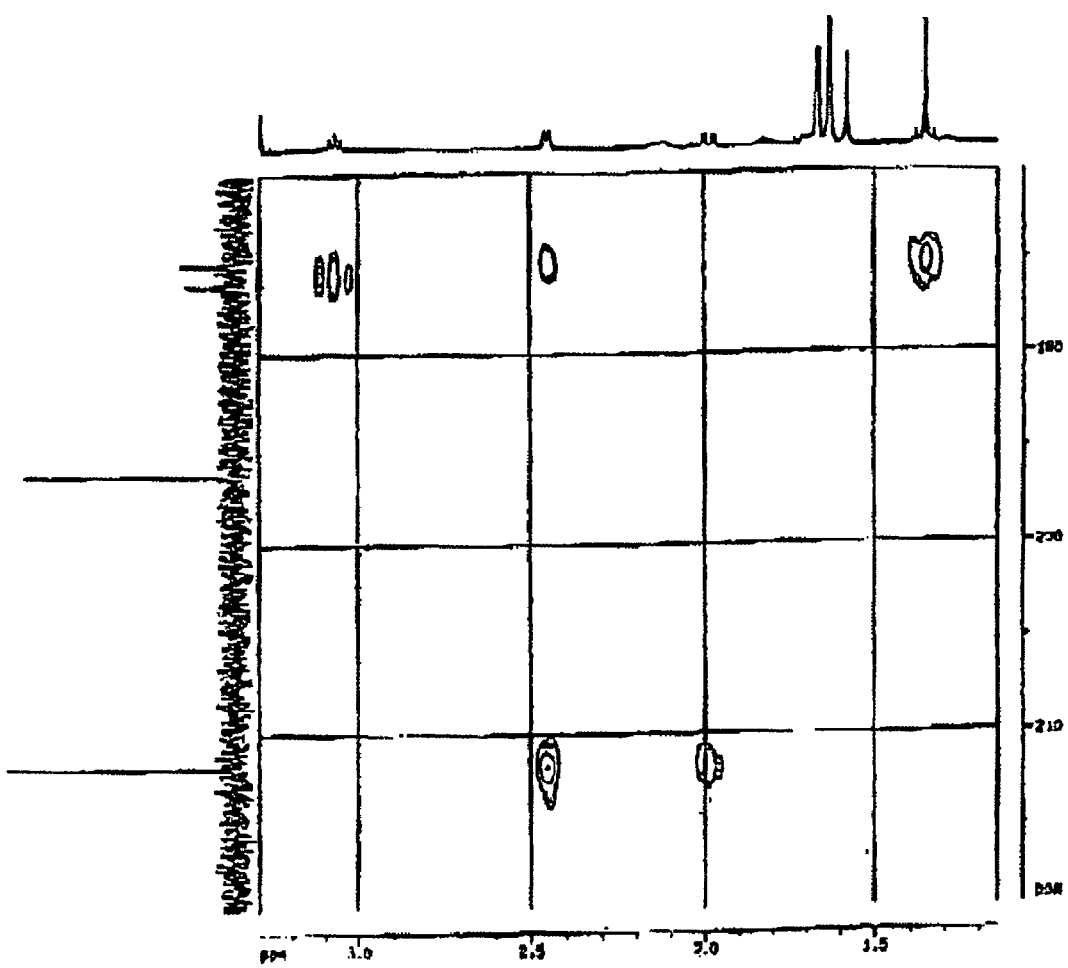
Figure 1M:
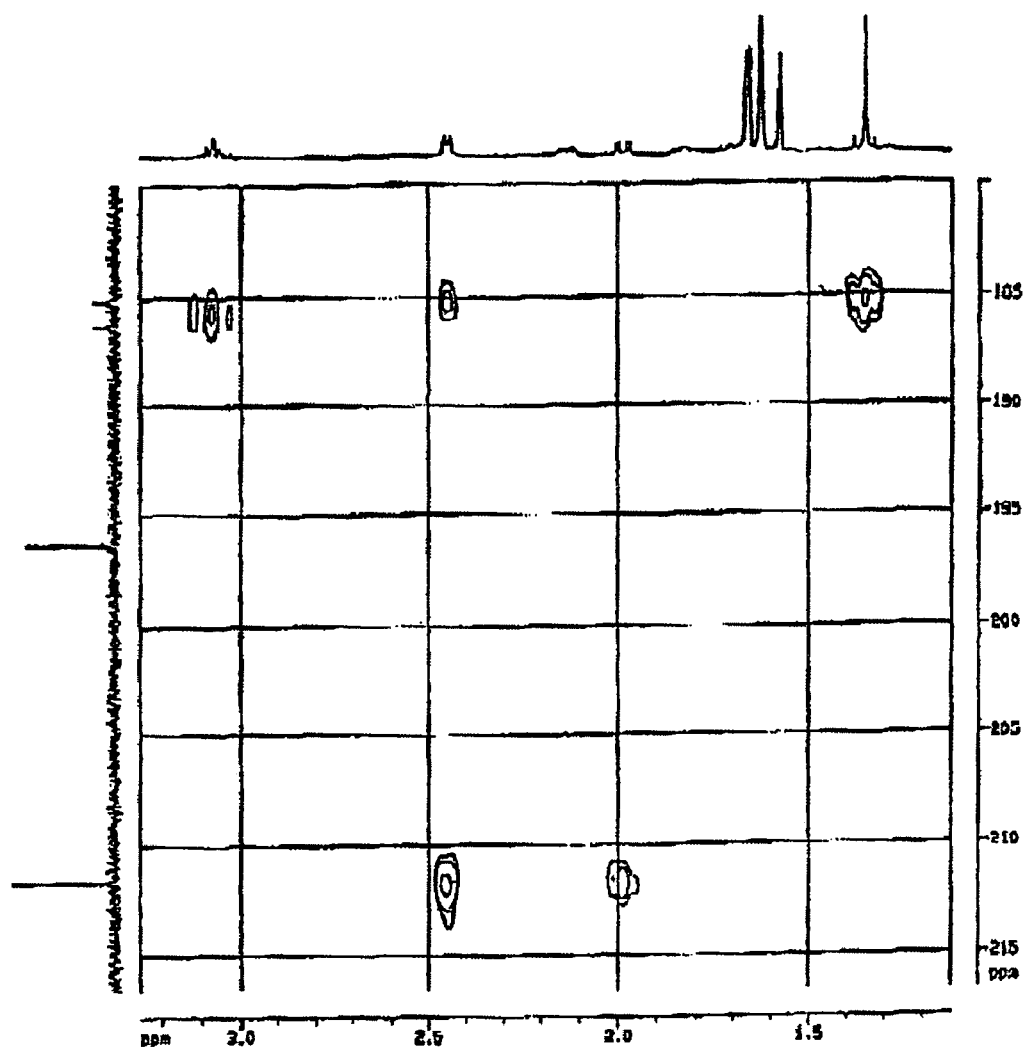
Figure 1N:
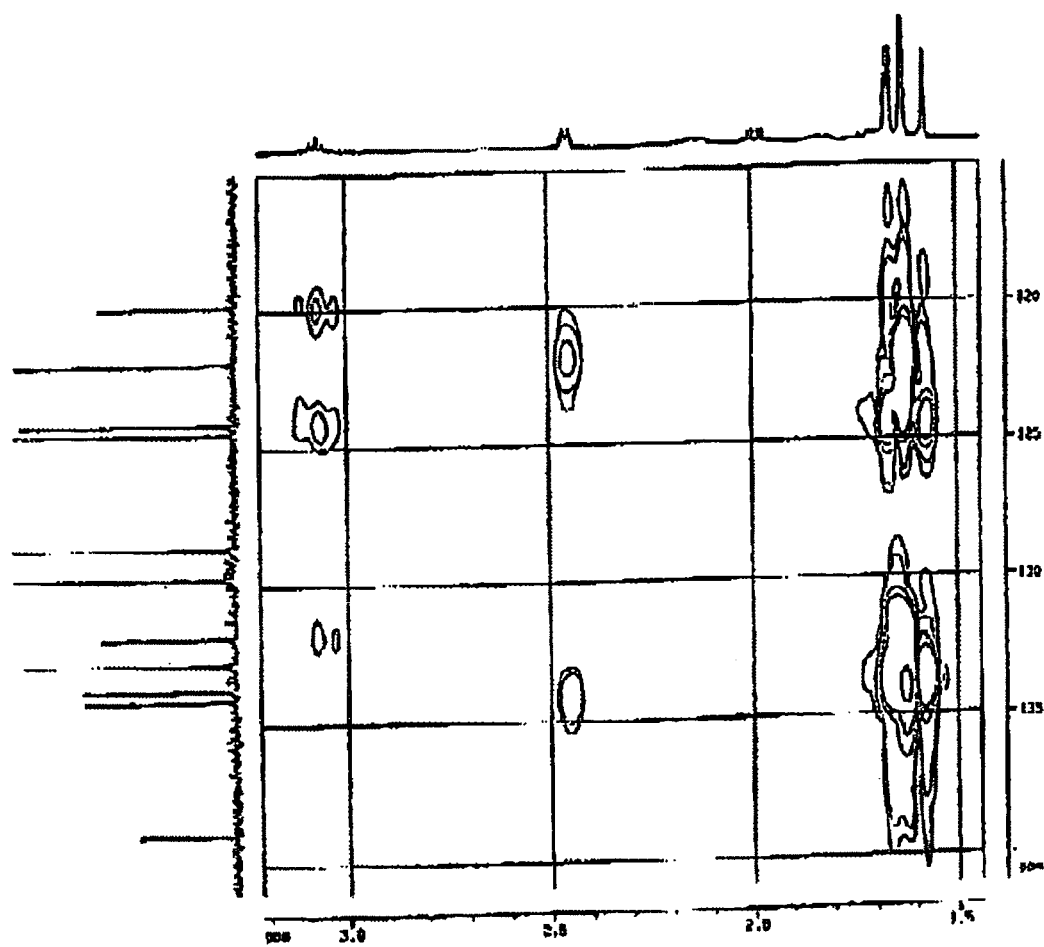
Figure 10:
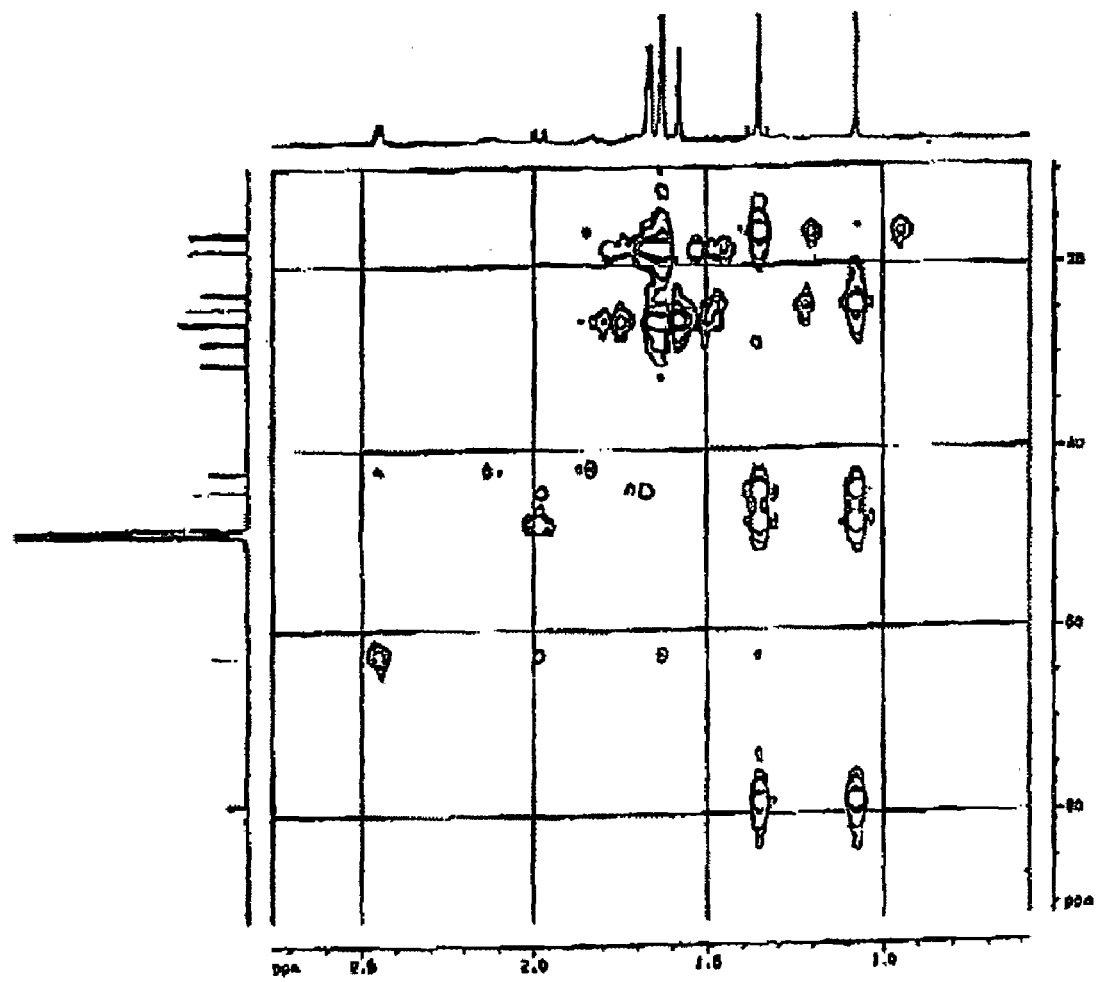
Figure 1P:
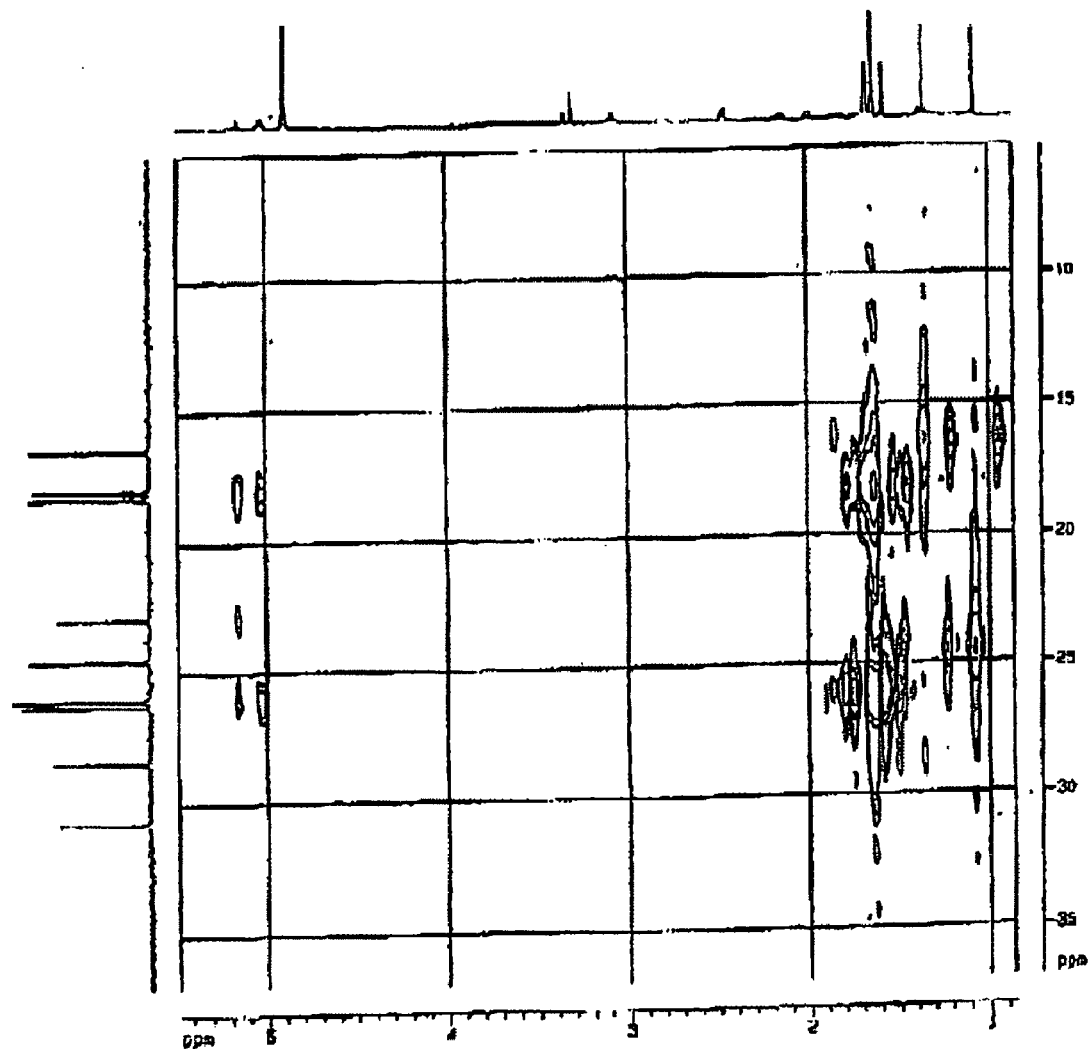
Figure 1Q:
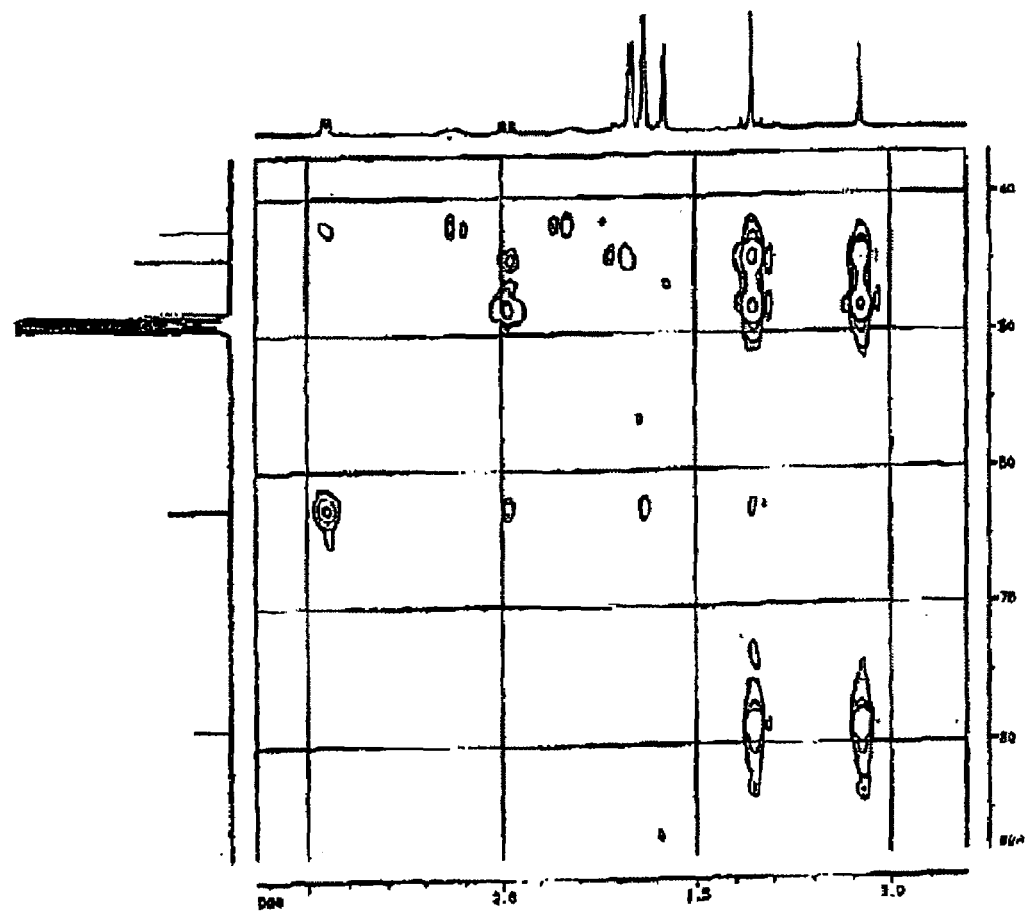
Figure 1R:
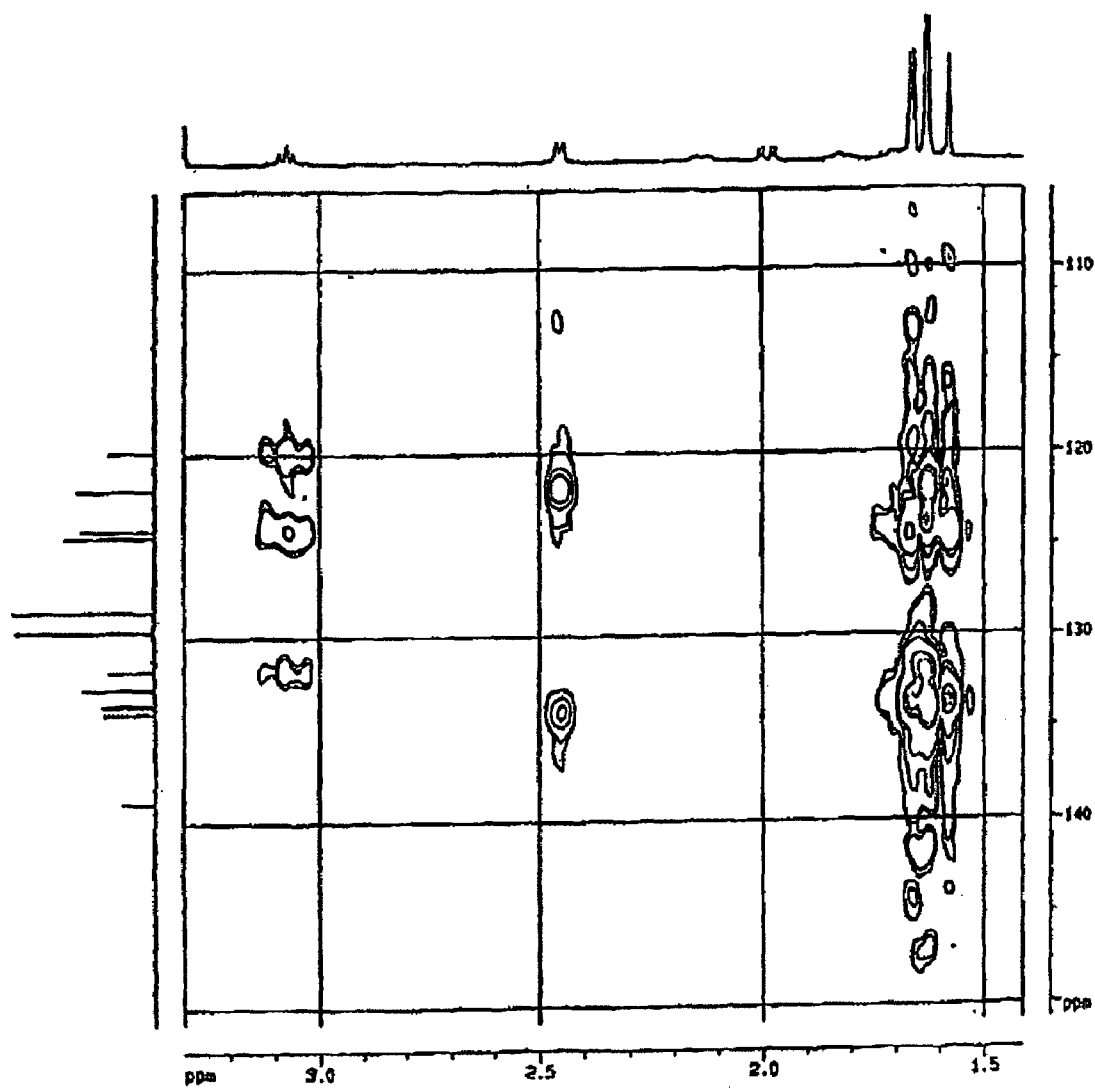

FIG. 1g depicts a $^{13}$C-DEPT spectrum of the compound (Ic') (measurement frequency: 125 MHz, solvent: $CD_3OD$); the CHs and CH$_3$s point upwards, while the CH$_2$s point downwards.

FIGS. 1h, 1i, 1j and 1k are H,H—COSY spectra of the compound (Ic') (measurement frequency: 500 MHz, solvent: $CD_3OD$).

FIG. 1l to 1r are HMBC spectra of the compound (Ic') (measurement frequency: 125 MHz, solvent: $CD_3OD$).

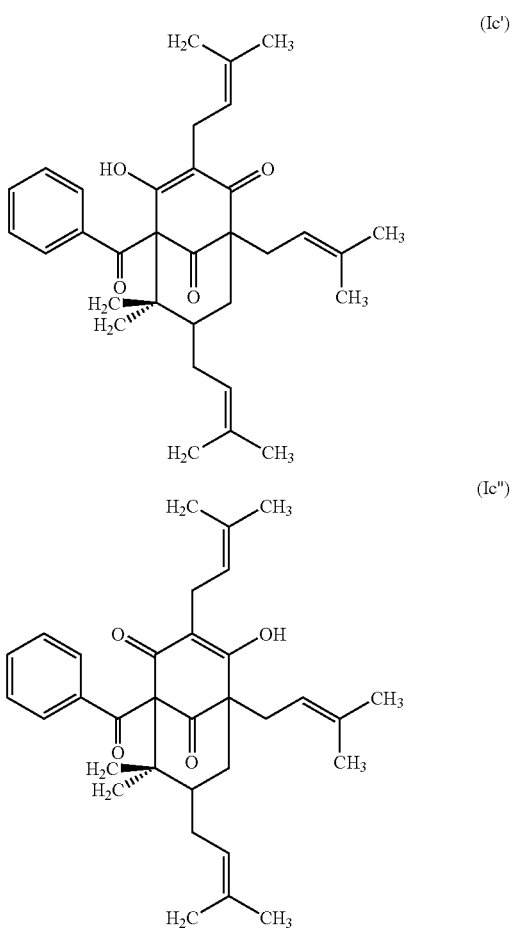

TABLE 1a

NMR data for the compound (Ic')
Compound of the formula (Ic') in $CD_3OD$

| C# | δ $^{13}$C, ppm | HMBC correl. with H# | δ $^1$H, ppm |
|---|---|---|---|
| 1 | 78.75 | 27, 28 | — |
| 2 | 186.30 (br) | 17 | — |
| 3 | 119.83 | 17 | — |
| 4 | 185.20 (br) | 22, 17, 6a | — |
| 5 | 62.74 | 22, 6a, 6e | — |
| 6 | 42.34 | 7, 22, 29 | 1.98 (1H, dd, 4.5 & 13.1 Hz, eq) |
|   |   |   | 1.35 (1H, t, overlap, 13.1 Hz, ax.) |
| 7 | 44.46 | 27, 28 | 1.83 |
| 8 | 48.24 | 6e, 27, 28 | — |
| 9 | 211.72 | 22, 6e | — |
| 10 | 196.39 | 12, 16 | — |
| 11 | 138.87 | 13, 15 | — |
| 12 | 129.66 | 14, 16 | 7.65 (1H) |
| 13 | 128.54 | 15 | 7.22 (1H) |
| 14 | 132.74 | 12, 16 | 7.39 (1H) |
| 15 | 128.54 | 13 | 7.22 (1H9 |
| 16 | 129.66 | 12, 14 | 7.65 (1H) |
| 17 | 22.9 | 18(w) | 3.10 (1H, dd, J = 14 & 7 Hz) |
|   |   |   | 3.05 (1H, dd, J = 14, & 7 Hz) |
| 18 | 124.07 | 17(w), 20, 21 | 5.15 (1H, tm, J = 7 & 1.4 Hz) |
| 19 | 131.81 | 20 | — |
| 20 | 26.26 | 18, 21 | 1.68 (3H, s) |
| 21 | 17.96 | 18, 20 | 1.63 (3H, s) |
| 22 | 30.73 |   | 2.47 (1H, dd, J = 15 & 7 Hz) |
|   |   |   | 2.44 (1H, dd, J = 15 & 7 Hz) |
| 23 | 121.88 | 22, 25, 26 | 5.02 (1H, m) |
| 24 | 134.09 | 22, 25, 26 | — |
| 25 | 26.03 | 23, 26 | 1.63 (3H, s) |
| 26 | 18.28 | 23, 25 | 1.63 (3H, s) |
| 27 | 24.51 | 28 | 1.35 |
| 28 | 16.42 | 27 | 1.08 |
| 29 | 28.42 |   | 2.13 (1H, m) |
|   |   |   | 1.70 (1H, m, overlap) |
| 30 | 124.41 | 32, 33 | 5.02 (1H, m) |
| 31 | 133.68 | 32, 33 | — |
| 32 | 26.05 | 30, 33 | 1.58 (3H, s) |
| 33 | 18.20 | 30, 32 | 1.67 (3H, s) |

H,H-COSY: H6a–H7, H6e–H7, H7–H29, H7–H29'
(w) = weak,
(br) = broad

Accordingly, the non-derivatized compound of the formula (Ic') or (Ic") or (Ic) exists in a keto/enol equilibrium, as confirmed both by the chemical shift of the signals and by the width of the $^{13}$C signals of C atoms 2 and 4.

TABLE 1b

NMR data for the methyl ether (II)
Compound of the formula (II) in $CDCl_3$

| C# | δ $^{13}$C, ppm | HMBC correl. with H# | δ $^1$H, ppm |
|---|---|---|---|
| 1 | 79.25 | 27, 28 | — |
| 2 | 194.07 | 17 | — |
| 3 | 126.80 | 17 | — |
| 4 | 173.07 | 17, 22, 6a, OMe | — |
| 5 | 59.81 | 22, 6a (w) | — |
| 6 | 40.22 | 22, 29 (w) | 2.00 (1H, dd, J=3.7 & 13.4 Hz, eq) |
|   |   |   | 1.45 (1H, dd, J=12.2 & 13.4 Hz, ax.) |
| 7 | 43.70 | 27, 28, 29, 6a (w) | 1.68 |
| 8 | 48.83 | 27, 28, 6e | — |
| 9 | 207.28 | 22, 6e | — |
| 10 | 193.06 | 12, 16 | — |
| 11 | 136.26 | 13, 15 | — |
| 12 | 128.57 | 14, 16 | 7.42 (1H) |
| 13 | 127.73 | 15 | 7.20 (1H) |
| 14 | 131.89 | 12, 16 | 7.35 (1H) |
| 15 | 127.73 | 13 | 7.20 (1H) |
| 16 | 128.57 | 12, 14 | 7.42 (1H) |
| 17 | 23.29 |   | 3.23 (1H, dd, J=15.2 & 6.9 Hz) |
|   |   |   | 3.14 (1H, dd, J=15.2 & 6.9 Hz) |

TABLE 1b-continued

NMR data for the methyl ether (II)
Compound of the formula (II) in CDCl$_3$

| C# | δ $^{13}$C, ppm | HMBC correl. with H# | δ $^1$H, ppm |
|---|---|---|---|
| 18 | 121.32 | 17, 20, 21 | 5.00 (1H, m) |
| 19 | 133.03 | 17, 20, 21 | |
| 20 | 26.02 | 18, 21 | 1.67 (3H, s) |
| 21 | 18.09 | 18, 20 | 1.63 (3H, s) |
| 22 | 29.78 | | 2.57 (1H, dd, J=14.3 & 7 Hz) |
| | | | 2.42 (1H, dd, J=14.3 & 7 Hz) |
| 23 | 119.51 | 22, 25, 26 | 5.00 (1H, m) |
| 24 | 134.36 | 22, 25, 26 | — |
| 25 | 25.68 | 23, 26 | 1.63 (3H, s) |
| 26 | 17.87 | 23, 25 | 1.61 (3H, s) |
| 27 | 23.42 | 28 | 1.33 (3H, s) |
| 28 | 15.72 | 27 | 1.11 (3H, s) |
| 29 | 26.72 | | 2.14 (broad) (1H, dd, 6.5 & 12.4 Hz) |
| | | | 1.70 (1H, overlap) |
| 30 | 122.58 | 32, 33 | 4.98 (1H, m) |
| 31 | 133.49 | 32, 33 | — |
| 32 | 25.79 | 30, 33 | 1.66 (3H, s) |
| 33 | 17.87 | 30, 32 | 1.56 (3H, s) |
| CH$_3$—O | 62.39 | | 3.99 (3H, s) |

H,H-COSY: H6a-H7, H7-H29
(w) = weak

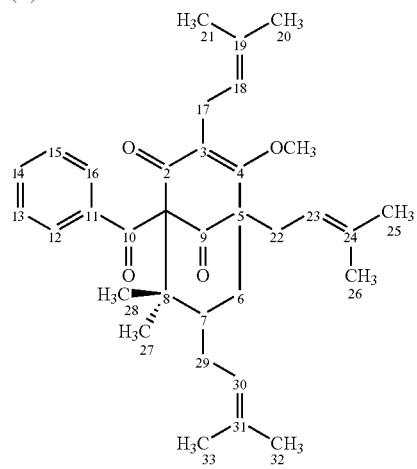

(II)

TABLE 1c

NMR data for the methyl ether (III)
Compound of the formula (III) in CDCl$_3$

| C# | δ $^{13}$C, ppm | HMBC correl. with H# | δ $^1$H, ppm |
|---|---|---|---|
| 1 | 73.97 | 27, 28 | — |
| 2 | 169.95 | 17, OMe | — |
| 3 | 123.22 | 17 | — |
| 4 | 197.14 | 17, 22, 6a | — |
| 5 | 65.17 | 7, 22 | — |
| 6 | 43.16 | 22, (w) | 1.925 (1H, dd, J=3.8 & 12.9 Hz, eq) |
| | | | 1.42 (1H, t, J=12.9 Hz, ax.) |
| 7 | 42.53 | 27, 28, 29, 6a | 1.66 |
| 8 | 47.86 | 27, 28, 6e | — |
| 9 | 207.91 | 22, 6e | — |
| 10 | 193.14 | 12, 16 | — |
| 11 | 137.03 | 13, 15 | — |
| 12 | 128.41 | 14, 16 | 7.59 (1H) |
| 13 | 127.94 | 15 | 7.28 (1H) |

TABLE 1c-continued

NMR data for the methyl ether (III)
Compound of the formula (III) in CDCl$_3$

| C# | δ $^{13}$C, ppm | HMBC correl. with H# | δ $^1$H, ppm |
|---|---|---|---|
| 14 | 132.08 | 12, 16 | 7.41 (1H) |
| 15 | 127.94 | 13 | 7.28 (1H) |
| 16 | 128.41 | 12, 14 | 7.59 (1H) |
| 17 | 23.25 | 18 (w) | 3.32 (1H, dd, J=15.7 & 6.8 Hz) |
| | | | 3.21 (1H, dd, J=15.7 & 6.8 Hz) |
| 18 | 121.54 | 17, 20, 21 | 4.97 (1H, m) |
| 19 | 133.02 | 17, 20, 21 | |
| 20 | 25.85 | 18, 21 | 1.66 (3H, s) |
| 21 | 18.02 | 18, 20 | 1.65 (3H, s) |
| 22 | 29.48 | | 2.55 (1H, dd, J=14 & 7 Hz) |
| | | | 2.45 (1H, dd, J=14 & 7 Hz) |
| 23 | 119.69 | 22, 25, 26 | 4.99 (1H, m) |
| 24 | 134.44 | 22, 25, 26 | — |
| 25 | 25.64 | 23, 26 | 1.66 (3H, s) |
| 26 | 18.15 | 23, 25 | 1.65 (3H, s) |
| 27 | 24.46 | 28 | 1.32 (3H, s) |
| 28 | 16.17 | 27 | 1.16 (3H, s) |
| 29 | 27.68 | | 2.07 (1H, m) |
| | | | 1.66 (1H, overlap) |
| 30 | 122.54 | 32, 33 | 4.89 (1H, m) |
| 31 | 133.23 | 32, 33 | — |
| 32 | 26.00 | 30, 33 | 1.65 (3H, s) |
| 33 | 17.86 | 30, 32 | 1.53 (3H, s) |
| CH$_3$—O | 61.54 | | 3.44 (3H, s) |

H,H-COSY: H6a-H7, H6e-H7, H7-H29
(w) = weak

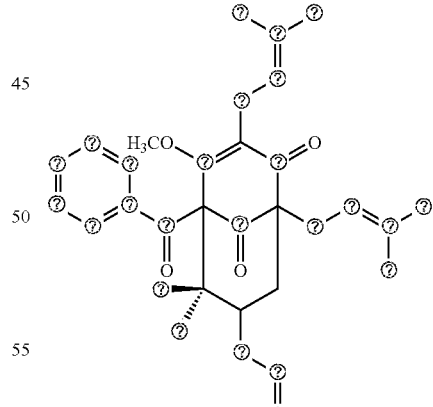

Ⓐ indicates text missing or illegible when filed (III)

Absolute Configuration

On the basis of the NMR data detailed above, it was possible to assign the following absolute configuration to the compound of the general formula (Ic) or (Ic') or (Ic"):

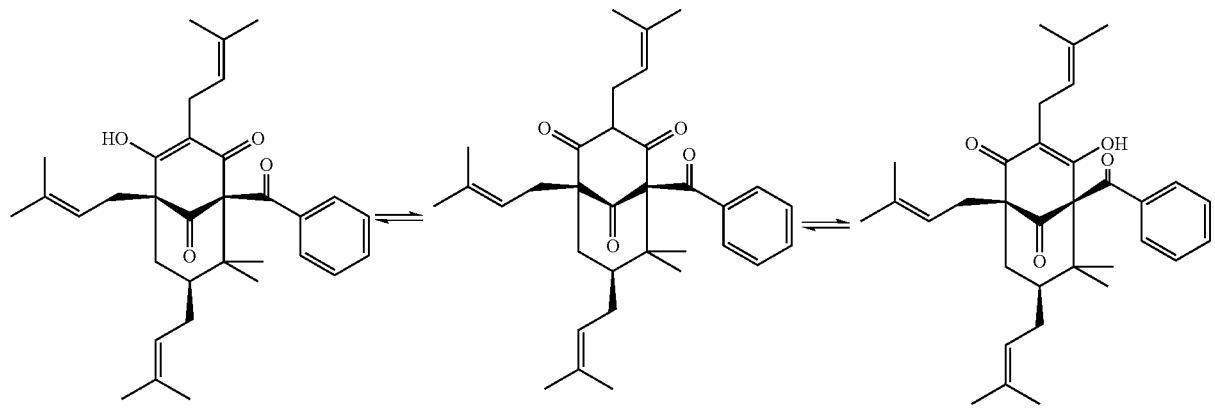

Cell Cultures

Six unambiguously characterized tumor cell lines of human origin (native cell lines and those converted into resistant subclones) and two non-tumor cell lines are used for further investigations (table 2).

TABLE 2

Cell lines, histological characterization of the cell lines and their origin

| Cell line | Histological characterization | RF | Source |
|---|---|---|---|
| M 51 | Carcinoma of stomach | | Hanover Medical |
| M51 DDP | Cisplatin resistant | 8.5 | Faculty |
| HT29 WT | Adenocarcinoma of colon | | ATCC HTB 38 |
| HT29 24R | 5-FU resistant | 3.7 | University of |
| HT29 SN38 | SN38 resistant | 3.6 | Essen Medical Faculty |
| HCT8 WT | Carcinoma of colon | | ATCC CCL24 |
| HCT8 SN38 | SN38 resistant | 6.9 | University of |
| HCT8 ICID | Raltitrexed resistant | 2.9 | Essen Medical Faculty |
| MCF-7 WT | Adenocarcinoma of breast | | ATCC HTB 22 |
| MCF-7 AD | Doxorubicin resistant gp 170+ | 222 | Roswell Park Cancer Institute |
| MCF-7 24R | 5-FU resistant | 6.5 | Roswell Park |
| A2780 WT | Adenocarcinoma of ovary | | Cancer Institute |
| A2780 DX5 | Doxorubicin resistant gp 170+ | 15.6 | Cancer Institute |
| A2780 CP2 | Cisplatin resistant | 15.0 | |
| H460 WT | Large-cell lung carcinoma | | ATCC HTB 117 |
| 3T3 | Mouse fibroblasts | | ATCC CCL 163 |
| MCR-5 | Diploid embryonic lung fibroblasts | | ATCC CCL 171 |

SRB Assay

The sensitivity of the cell lines to the substance (Ic') is determined in a so-called sulforhodamine B (SRB) assay. This is a robust and highly reproducible standard method which is also established for example at the NCI (National Cancer Institute, USA) (Skehan et al. 1990).

The results of the assays are shown in table 3. The concentration of substance (Ic') which inhibits cell growth by 50% ($IC_{50}$, determined from semilogarithmic dose versus effect plots) are indicated. The results shown in table 3 are averages and their standard deviations of at least three independent experiments. There is no cross-resistance to the indicated cytostatics. The cytotoxicity of the substance (Ic') for the non-tumor cell lines (fibroblasts of the 3T3 and MCR 5 lines) proves to be considerably less.

TABLE 3

Determined $IC_{50}$ concentrations of substance (I) in the various cell lines.

| Cell line | Substance (Ic') $IC_{50}$ (µg/ml) |
|---|---|
| M51 WT | 5.70 ± 0.21 |
| M51 DDP | 4.77 ± 0.13 |
| HT29 WT | 5.25 ± 0.43 |
| HT29 24R | 5.18 ± 0.76 |
| HT29 SN38 | 3.50 ± 1.40 |
| HCT8 WT | 4.23 ± 0.19 |
| HCT8 SN38 | 4.07 ± 0.08 |
| HCT8 ICID | 4.44 ± 0.13 |
| MCF-7 WT | 4.37 ± 0.12 |
| MCF-7 AD | 4.28 ± 0.08 |
| MCF-7 24R | 3.30 ± 0.51 |
| A2780 WT | 9.20 ± 0.82 |
| A2780 DX5 | 6.75 ± 1.55 |
| A2780 CP2 | 6.23 ± 0.12 |
| H460 WT | 4.21 ± 0.91 |
| 3T3 | >80.0 |
| MCR-5 | 21.73 ± 6.47 |

Investigations of Topoisomerase I Inhibition

The effect of the substance (Ic') on topoisomerase I is investigated by carrying out the so-called Topo I unwinding assay. The assay is based on an ATP-independent unwinding of twisted pBR322 plasmid DNA dimers by topoisomerase I. The two different topological forms of the plasmid DNA, the twisted form and unwound, relaxed form, are separated in this investigation by means of an agarose gel. The enzyme topoisomerase I is obtained for this purpose from cell nucleus extracts of the tumor cell lines.

Obtaining Cell Nucleus Extracts

Cell nucleus extracts are obtained by the method of Sullivan with the modifications of Danks et al.

Inhibition of Topoisomerase I Activity by Substance (Ic')

As shown in FIG. 2 (column 1: controls), 160 ng of cell nucleus extract with the topoisomerase I present therein are required in order to convert the highly twisted pBR322 plasmid DNA dimers (negative control) into the relaxed topology (positive control). The substance (Ic') inhibits topoisomerase I activity 100% at a concentration of 100 µg/ml. This corresponds to 20 times the concentration required to inhibit the tumor growth of the corresponding cell lines by 50%. Comparison of the data with the in vitro inhibitory activity of, for example, topotecan shows 1000 times the $IC_{50}$ is required for this substance which is already clinically established. FIG. 2 illustrates the inhibition of topoisomerase I activity by substance (Ic').

Cell Cycle Analyses

The effects described to date for substance (Ic') on cell growth can also be demonstrated by changes in the cell cycle. Flow cytometric investigations by an adapted method of Tsugita M. et al. are used for the analysis.

Exponentially growing HCT8 WT bowel cancer cells are treated with substance (Ic') with the determined $IC_{50}$ concentration for 24 hours, and then the cells are incubated with BrdU. The cells fixed with methanol are subjected to a treatment with a detergent (Triton X-100/HCl) in order to denature the DNA strands. After incubation with the fluorescence-labeled antibody (anti-BrdU mAb, FITC-labeled), the second fluorescent dye (PI, propidium iodide) is added.

The DNA content (propidium iodide fluorescence) and the amount of BrdU taken up (FITC fluorescence) are determined using a Coulter flow cytometer (Coulter EPICS XL). Exemplary results are depicted in FIG. 3a and 3b.

FIG. 3a and 3b show BrdU and PI uptakes into the DNA of HCT8 WT cells, untreated (control, FIG. 4a) and treated with substance (Ic') ($IC_{50}$, 24 hours, FIG. 4b). The depicted results are representative of n=3 independent experiments.

It is evident that treatment with substance (Ic') leads to inhibition of the synthesis phase. This is clear from the figures on the DNA content (FIG. 3a and 3b, BrdU uptake).

Analysis of DNA Degradation

The investigations to demonstrate degradation of DNA by substance (Ic') are carried out by way of example on human cells of a bronchial carcinoma (H460 WT) and of a colorectal carcinoma (HT29 WT). DNA isolated after treatment of the cells for various times with substance (Ic') is for this purpose analyzed by gel electrophoresis.

Determination of the DNA double-strand breaks is performed on $^{14}C$-labeled DNA. For this purpose, $[^{14}C]$d-thymidine-labeled cells are treated with various concentrations of substance (Ic'). The DNA is isolated by an adapted method of Chia Chiao et al.

After determining the amount and purity of the isolated DNA using a GeneQuant spectrophotometer, comparable amounts of DNA are fractionated using an agarose gel. The DNA fractionated by gel electrophoresis is subsequently stained with ethidium bromide.

On a transilluminator (302 nm), the intact DNA which has not migrated in the electric field is separated from the fragmented DNA, which has thus migrated into the gel, by extraction. The isolated gel and DNA fragments are liquefied at +80° C. in the presence of hydrochloric acid. After addition of a scintillator it is possible to determine the radioactivity using a liquid scintillation meter (TPI-CARB 2100RT). The measured radioactivity is indicated in disintegrations per minute (cpm).

Figure 4:
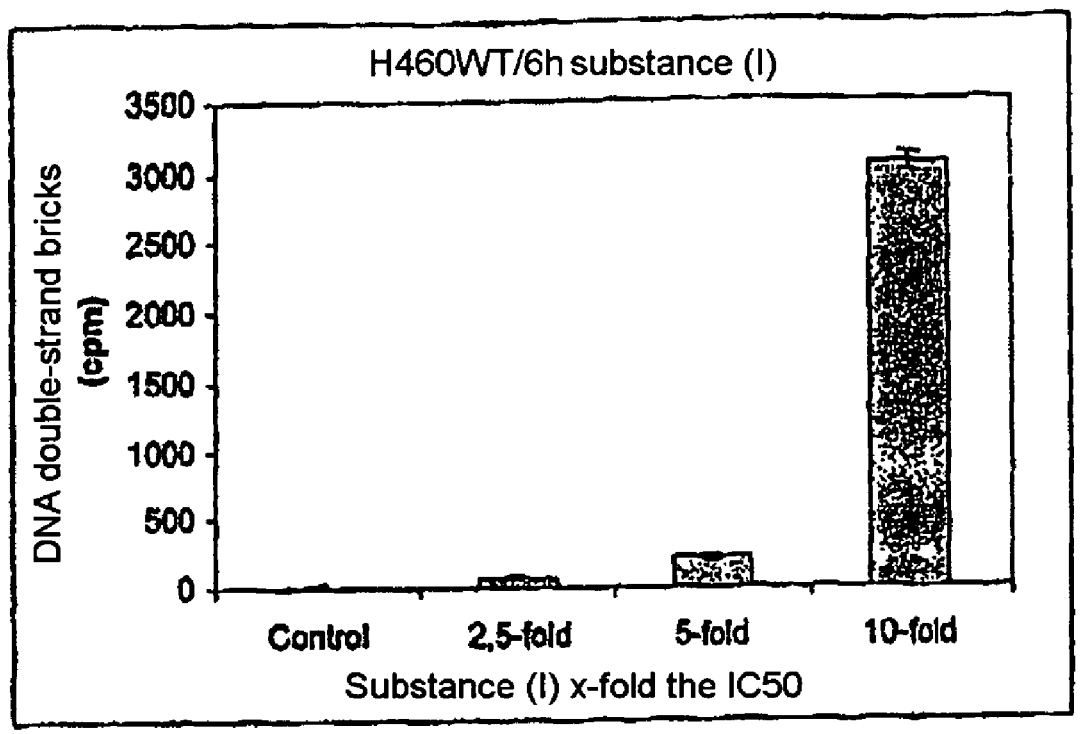

FIG. 4 shows the induction of double-strand breaks by substance (Ic') after incubation of bronchial carcinoma cells (H480 WT) for 6 hours. FIG. 4 shows DNA double-strand breaks detected in $[^{14}C]$d-Thy-labeled H460 WT cells induced by the treatment with substance (Ic') for 6 hours. The results represent averages and their standard deviation from n=3 independent experiments.

The treatment of the tumor cells with up to 10 times the determined $IC_{50}$ concentration over the course of 6 hours induces significant amounts of double-strand breaks which evidently are not sufficiently repaired by the tumor cells, even at the $IC_{50}$ concentration, and thus induce cell death.

Figure 5:
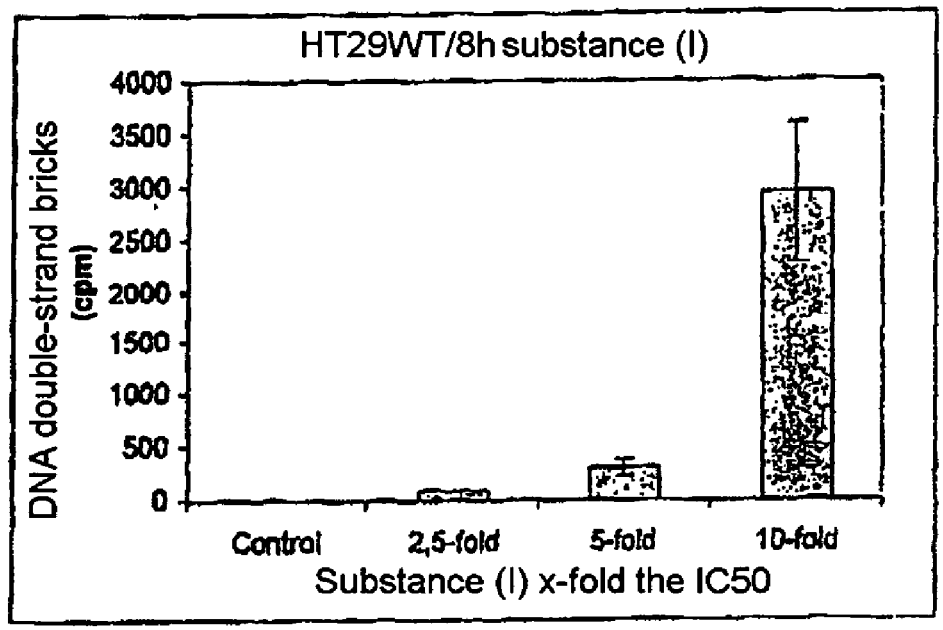

FIG. 5 shows a further example of the induction of double-strand breaks in the DNA of tumor cells, in this case cells of a colorectal tumor (HT29 WT). As for the bronchial carcinoma cell line, there is evidently induction of substantial amounts of double-strand breaks which cannot be corrected again by the repair mechanism of the tumor cell and eventually represents a contributory factor to inducing apoptosis, the programmed cell death, of the tumor cell.

Determination of the Inhibitory Activity of Substance (Ic') on Human Telomerase

The effect of substance (Ic') on human telomerase is determined by carrying out the so-called Telomeric Repeat Amplification Assay (TRAP) ELISA, based on the method of N. W. Kim et al.

This method is based on use of the polymerase chain reaction (PCR). This entails, in a first step, a number of (GGTTAG) motifs being attached by means of the telomerase activity to the 3' end of a biotin-labeled oligonucleotide (TS=telomerase substrate). In a second step, the products extended in this way are amplified by the PCR technique using TS and RP (R=reverse) primers. In this way, a "ladder" of products in increments of 6 bases (initial size=50 nucleotides) is generated. During the amplification, DNP-labeled dCTP is incorporated into the PCR products. Detection and quantification of the synthesized telomerase products using a sandwich ELISA method are a measure of the telomerase enzymatic activity.

The telomerase products carry the biotin-labeled TS primers and bind to the surface of microtiter plates previously coated with streptavidin. An anti-DIG antibody conjugated to POD binds to the DNP-labeled nucleotides incorporated during the amplification. After addition of the substrate TMB, the telomerase activity is visualized by fluorescence spectroscopy via the onset of the color reaction by the enzyme POD. In this case, the measured absorption is directly proportional to the telomerase activity.

Effect of Substance (Ic') on the Activity of Human Telomerase

In order to ensure the effect of substance (Ic') on telomerase, an effect of substance (Ic') on DNA polymerase must be ruled out. In a preliminary experiment with TSR8 as internal control, the effect of substance (Ic') at various concentration levels was ruled out.

Amplification of the TSR8 template depends only on DNA polymerase. Every inhibitor of this enzyme can be detected using the substrate.

Figure 6:
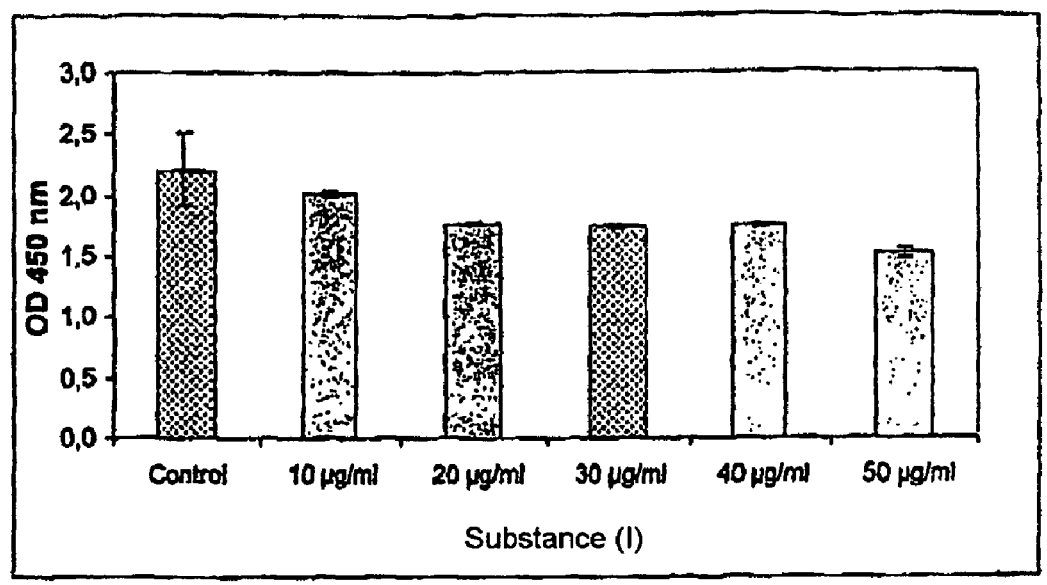

FIG. 6 shows the results of the preliminary experiment with the TSR8 template. The experiment is carried out in triplicates. FIG. 6 demonstrates that even the maximum concentration employed of substance (Ic'), 50 µg/ml, in this experiment does not lead to a significant inhibition of Taq polymerase.

Figure 7:
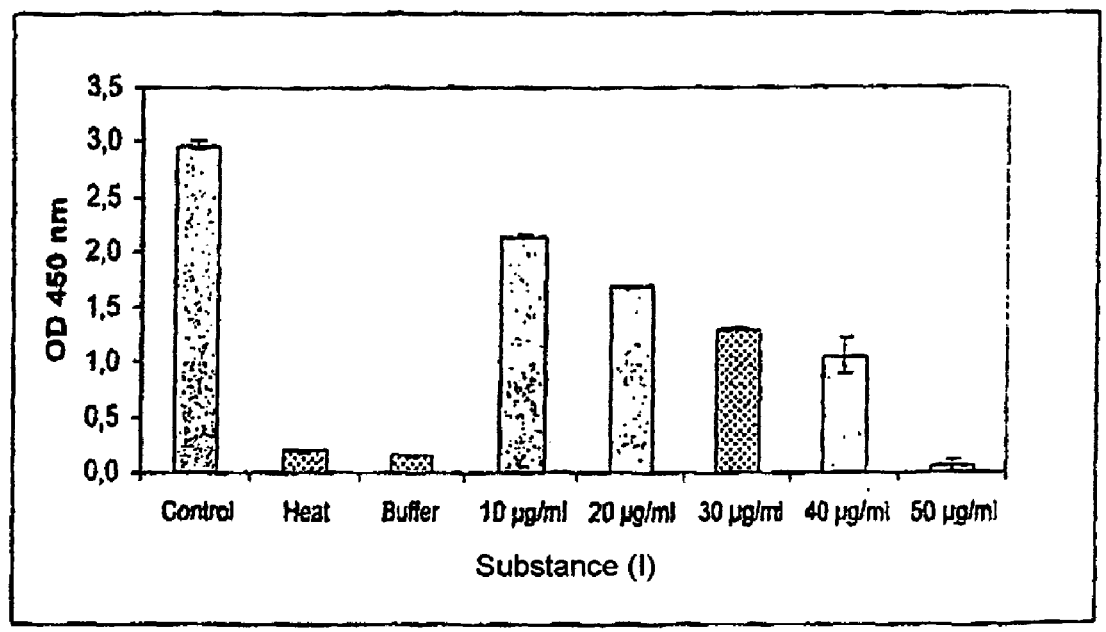

The experiment to investigate telomerase inhibition by substance (Ic') is shown in FIG. 7. The concentration range between 10 and 50 µg/ml is depicted. Complete inhibition of human telomerase is observed at a concentration of 50 µg/ml.

FIG. 7 shows the results of the TRAP assay: dose-dependent inhibition of human telomerase obtained from cells of a colon carcinoma (HCT8 WT) by substance (Ic'). The results represent averages and standard deviations of three independent experiments.

Figure 8:
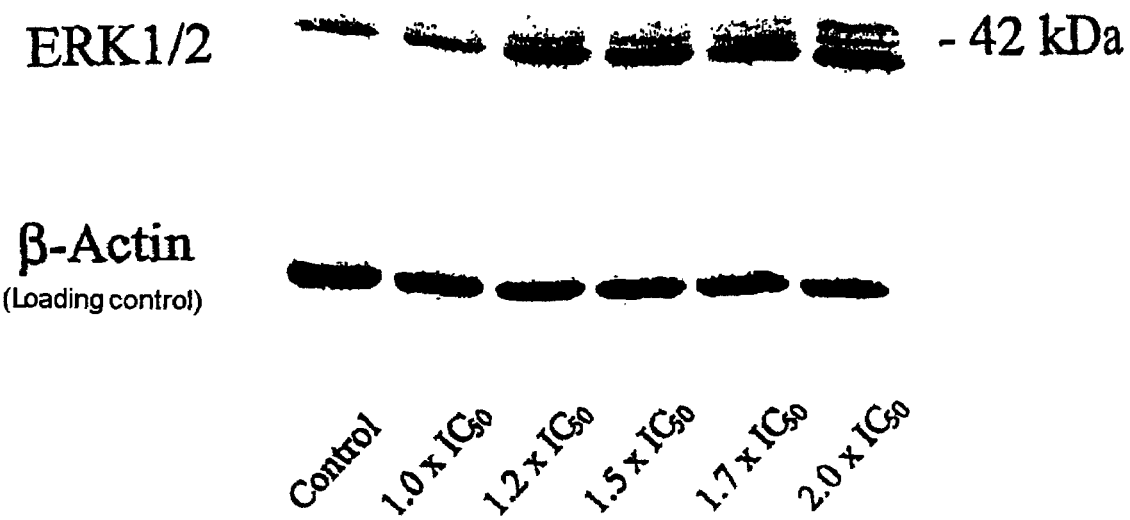
FIG. 8 shows the Western blot analysis of the ERK1/2 protein; the loading control is included in the lower line.

The experiment to investigate telomerase inhibition by substance (Ic') is shown in FIG. 8. The concentration range between 10 and 50 µg/ml is depicted. Complete inhibition of human telomerase is observed at a concentration of 50

μg/ml. FIG. 8 shows the results of the TRAP assay: dose-dependent inhibition of human telomerase obtained from cells of a colon carcinoma (HCT8 WT) by substance (Ic'). The results represent averages and standard deviations of three independent experiments.

Phosphorylation of ERK1/2 (MAP Kinase Pathway)

Phosphorylation of certain signal transduction pathways plays an essential role in the regulation of cell growth and gene expression. The protein ERK1/2 (MAP kinase) belongs to the MAP kinase signal transduction pathway.

Treatment of human colon carcinoma cells (HCT8 WT) with substance (Ic') leads to phosphorylation of this protein, which is detected in a Western blot analysis (FIG. 8). FIG. 8 shows the Western blot analysis of the ERK1/2 protein; the loading control is included in the lower line.

Treatment of the cells with substance (Ic') leads to dose-dependent phosphorylation of the ERK1/2 protein. Even at a dose corresponding to the $IC_{50}$ it is possible to demonstrate phosphorylation by substance (Ic'). As a result of this process—to date interpreted in the literature as activation—the tumor cell is consigned to cell cycle arrest, which is demonstrated by the cell cycle analyses carried out (see above).

Figure 9:
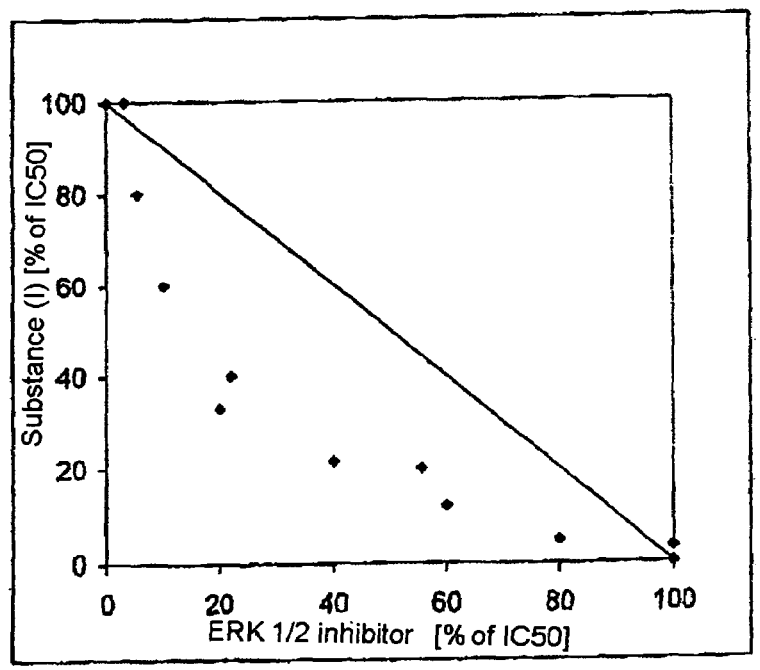
FIG. 9 represents the coincubation experiment on the cytotoxicity with substance (Ic') and a specific ERK1/2 inhibitor (MAP kinase inhibitor). HCT8 WT cells were coincubated.

To check these findings, how far the results obtained for ERK1/2 activation by substance (Ic') can be antagonized by adding an ERK1/2 inhibitor, a coincubation experiment is carried out with substance (Ic') and a specific ERK1/2 inhibitor (MAP kinase inhibitor). In this case, tumor cells, e.g. colon carcinoma cells (HCT8 WT), are coincubated with both active ingredients in different dosages in each case for 24 hours (FIG. 9). FIG. 9 represents the coincubation experiment on the cytotoxicity with substance (Ic') and a specific ERK1/2 inhibitor (MAP kinase inhibitor). HCT8 WT cells were coincubated. The points shown indicate the corresponding ratios (% of the respective $IC_{50}$ concentration) of the two active ingredients to one another.

However, this experiment carried out in such a way leads to no abolition of the measured cytotoxicity in any dosage ratio. On the contrary, a pronounced synergism on coincubation of the two active ingredients is evident.

All dosage combinations are below the angle bisectors and thus in the range of unambiguous synergism. Combination of 30% of the $IC_{50}$ concentration of substance (Ic') with an active ingredient concentration of 30% of the $IC_{50}$ concentration of the specific ERK1/2 inhibitor leads to inhibition of growth of the tumor cells isolated from a colon carcinoma (HCT8 WT).

The invention claimed is:

1. A pharmaceutical combination, comprising:
   (A) at least one substituted bicyclo[3.3.1]nonane-2,4,9-triones compound of the general formula (I)

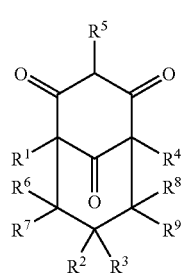

in which:
   $R^1$, $R^2$, $R^4$ and $R^5$, identical or different, are independently of one another one of the following groups:

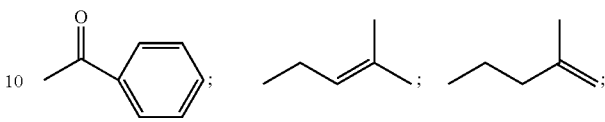

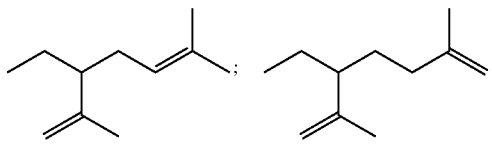

but with the proviso that if one of the radicals $R^1$ or $R^2$ or $R^4$ or $R^5$ is a benzoyl group, none of the other of these radicals is a benzoyl group;

$R^3$ is a hydrogen atom;

$R^6$ and $R^7$ are both in each case a methyl group or else in each case a hydrogen atom, and $R^8$ and $R^9$ are both in each case a methyl group or else in each case a hydrogen atom, but with the proviso that if $R^6$ and $R^7$ are methyl groups, $R^8$ and $R^9$ are hydrogen atoms, and that if $R^8$ and $R^9$ are methyl groups, $R^6$ and $R^7$ are hydrogen atoms;

and/or its physiologically tolerated salts, hydrates, isomers, in particular stereoisomers, tautomers and structural isomers, derivatives, prodrugs and metabolites; and (B) at least one further chemotherapeutic agent, comprising a protein kinase inhibitor.

2. The pharmaceutical combination as claimed in claim 1, wherein components (A) and (B) are present either as functional unit, in the form of a mixture, a mix or a blend, or else (spatially) separate from one another.

3. The pharmaceutical combination as claimed in claim 1 or 2, wherein components (A) and (B) can be used or administered either simultaneously or else sequentially.

4. The pharmaceutical combination as claimed in claim 2, comprising components (A) and (B) each in therapeutically effective amounts.

5. The pharmaceutical combination as claimed in claim 1 for systemic and/or topical use.

6. A medicament for the prophylactic and/or therapeutic treatment of a viral disease comprising the pharmaceutical combination of claim 1.

7. The pharmaceutical combination as claimed in claim 1, wherein the protein kinase inhibitor comprises MAP kinase inhibitor.

* * * * *